United States Patent [19]
Cook

[11] Patent Number: 5,700,922
[45] Date of Patent: Dec. 23, 1997

[54] PNA-DNA-PNA CHIMERIC MACROMOLECULES

[75] Inventor: Phillip Dan Cook, Carlsbad, Calif.

[73] Assignee: Isis Pharmaceuticals, Inc., Carlsbad, Calif.

[21] Appl. No.: 158,352

[22] Filed: Nov. 24, 1993

Related U.S. Application Data

[63] Continuation-in-part of PCT/US92/11339, Dec. 23, 1992, which is a continuation-in-part of Ser. No. 814,961, Dec. 24, 1991, abandoned.

[51] Int. Cl.$^6$ .............................. C07H 21/02; C07H 21/04
[52] U.S. Cl. ........................... 536/23.1; 514/44; 435/91.1; 435/91.5; 536/23.5; 536/24.1; 536/24.2; 536/24.33; 536/25.1; 536/25.2; 536/25.3; 536/25.31; 536/24.5; 536/24.31; 536/24.32; 935/5; 935/8
[58] Field of Search .......................... 514/44; 435/91.1, 435/91.5; 536/23.5, 24.1, 24.2, 24.33, 25.1, 25.2, 25.3, 25.31, 24.5, 24.31, 24.32

[56] References Cited

U.S. PATENT DOCUMENTS

| | | | |
|---|---|---|---|
| 3,687,808 | 8/1972 | Merigan, Jr. et al. | 435/91.3 |
| 4,908,307 | 3/1990 | Rodland et al. | 435/6 |
| 5,013,830 | 5/1991 | Ohtsuka et al. | 536/25.1 |
| 5,134,066 | 7/1992 | Rogers et al. | 435/91.3 |
| 5,149,797 | 9/1992 | Pederson et al. | 536/23.1 |

FOREIGN PATENT DOCUMENTS

| | | |
|---|---|---|
| 2017369 | 11/1990 | Canada . |
| 0 260 032 | 3/1988 | European Pat. Off. . |
| 0 339 842 | 11/1989 | European Pat. Off. . |
| 0 339 330 | 11/1990 | European Pat. Off. . |
| 39 15 462 A1 | 9/1990 | Germany . |
| 41 10 085 | 10/1992 | Germany . |
| 3-240795 | 10/1991 | Japan . |
| WO 86/05518 | 9/1986 | WIPO . |
| WO 90/15814 | 12/1990 | WIPO . |
| WO 91/06556 | 5/1991 | WIPO . |
| WO 91/12323 | 8/1991 | WIPO . |
| WO 91/15499 | 10/1991 | WIPO . |
| PCT/EP92/ 01219 | 5/1992 | WIPO . |
| WO92/20703 | 11/1992 | WIPO . |
| WO 93/13121 | 12/1992 | WIPO . |

OTHER PUBLICATIONS

Jasenka Matulic–Adamic, et al., "Nucleosides. 150. Synthesis and Some Biological Properties of 5–Monofluoromethyl, 5–Difluoromethyl, and 5–Trifluoromethyl Derivatives of 2'–Deoxyuridine and 2'–Deoxy–2'–fluoro–β–D–arabinofuranosyluracil", *J. Med. Chem.*, 31, (1988), 1642–1647.

Wu–Pong, "Oligonucleotides: Opportunities for Drug Therapy and Research", *Pharmaceutical Technology* 1994, 102.

Agrawal et al., "Oligodeoxynucleoside Phosphoramidates and Phosphorothioates as Inhibitors of Human Immunodeficiency Virus", PNAS USA 85: 7079–7083 (1988).

Akashi, M. and Takemoto, K. "New Aspects of Polymer Drugs", Adv. Polym. Sci., 1990, 97, 108–146.

Beaton, et al., Chapter 5, Synthesis of oligonucleotide phosphorodithioates, p. 109, *Oligonucleotides and Analogs, A Practical Approach*, Eckstein, F., Ed.; The Practical Approach Series, IRL Press, New York, 1991.

Borer et al., "Stability of Ribonucleic Acid Double–Stranded Helices", *J. Mol. Biol.* 86: 843–853 (1974).

Brill et al., "Synthesis of Deoxydinucleotide Phosphorodithioates", 3972–3980, The Journal of the American Chemical Society 113: 3972–3980 (1991).

Buttrey, J.D., et. al. "Synthetic Analogues of Polynucleotides–XIII, The Resolution of DL–β–(Thymin–1–YL)Alanine and Polymerisation of the β–(Thymin–1–YL) Alanines", Tetrahedron, 1975, 31, 73–75.

Capon et al., "Complete Nucleotide Sequences of the T24 Human Bladder Carcinoma Oncogene and Its Normal Homologue", *Nature* 302: 33–37 (1983).

Cohen, "Oligodeoxynucleotides" Published 1989 by CRC Press, Inc., Boca Raton (FL) pp. 1–255 Note pp. 16, 35, 36, 38, 55, 62, 66, 67, 79–82, 85.

Concise Encyclopedia Of Polymer Science And Engineering, J.I. Kroschwitz, Ed. John Wiley & Sons, 1990 at pp. 858–859.

Dagle et al., "Targeted Degradation of mRNA in xenopus Oocytes and Embryos directed by modified oligonucleotides: Studies of An2 and Cyclin in Embryogenesis", Nucleic Acid Research 18: 4751–4757 (1990).

Dagle, et al., "Physical Properties of Oligonucleotides Containing Phosphoramidate–Modified Internucleoside Linkages", Nucleic Acids Research 19: 1805–1810 (1991).

Dagle et al, "Pathways of Degradation and Mechanism of Action of Antisense Oligonucleotidews in Xenopus Laevis Embryos", Antisense Research and Development, No. 1: 11–20 (1991).

De Koning, H., et. al. "Unconventional Nucleotide Analogues V. Derivatives of 6–(1–pyrimidinyl)–and 6–(9–purinyl)–2–aminocaproic acid.", Recueil, 1971, 90, 874–884.

Demidov et al., "Sequence Selective Double Strand DNA Cleavage by Peptide Nucleic Acid (PNA) Targeting Using Nuclease S1", Nucl. Acids Res 21 (19): 2103–2107 (1993).

Depto et al., "Regulated Expression of the Human Cytomegalovirus pp65 Gene: Octamer Sequence in the Promoter Is Required for Activation by Viral Gene Products," *J. Virol.*, 1989, 63:1232–1238, 1989.

(List continued on next page.)

*Primary Examiner*—Christopher S. F. Low
*Attorney, Agent, or Firm*—Woodcock Washburn Kurtz Mackiewicz & Norris LLP

[57] ABSTRACT

Macromolecules are provided that have increased nuclease resistance, increasing binding affinity to a complementary strand, and that activate RNase H enzyme. The macromolecules have the structure PNA-DNA-PNA where the DNA portion is composed of subunits of 2'-deoxy-erythro-pentofuranosyl nucleotides and the PNA portions are composed of subunits of peptide nucleic acids. Such macromolecules are useful for diagnostics and other research purposes, for modulating protein in organisms, and for the diagnosis, detection and treatment of other conditions susceptible to therapeutics.

23 Claims, 6 Drawing Sheets

OTHER PUBLICATIONS

Doel, M.T., et. al. "The Synthesis of Peptides Containing Purine and Pyrimidine Derivatives of DL-Alanine", Tetrahedron 30: 2755–2759 (1974).

Doel, M.T., et. al. "An Approach to the Synthesis of Peptide Analogues of Oligonucleotides (Nucleopeptides)", Tetrahedron Letters 27: 2285–2288 (1969).

Dubochet et al., "A New Preparation Method for Dark–Field Electron Microscopy of Biomacromolecules," *J. Ultrastruct. Res.* 35: 147–167 (1971).

Egholm, "Peptide Nuleice Acids Containing Adenine or Guanine Recognize Thymine and Cytosine in Complementary DNA Sequences", J. Chem. Soc., Chem. Commun. 800–801 (1993).

Egholm et al., "Peptide Nucleic Acids (PNA). Oligonucleotide Analogues with an Achiral Peptide backbone," *J. Am. Chem. Soc.* 114: 1895–1897 (1992).

Englisch, U. and Gauss, D.H., "Chemically Modified Oligonucleotides as Probes and Inhibitors", *Angewandte Chemie*, International Edition 30: 613–629 (1991).

Froehlder et. al., "Oligodeoxynucleotides Containing C–5 Propyne Analogs of 2'–Deoxyuridine and 2'–Deoxycytidine," *Tetrahedron Letters* 33: 5307–5310 (1992).

Hahn et. al., "Molecular cloning and characterization of the HTLV–III virus associated with AIDS," *Nature*, 312:166–169, 1984.

Hall and Brown, "Human N–ras: cDNA Cloning and Genes Structure", *Nucleic Acids Res.* 13: 5255–5268 (1985).

Hanvey, J.C., et. al. "Antisense and Antigene Properties of Peptide Nucleic Acids", Science 258: 1481–1485 (1992).

Huang, S., et. al. "Acyclic Nucleic Acid Analogues: Synthesis and Oligomerization of γ,4–Diamino–2–oxo–1 (2H)–pyrimidinepentanoic Acid of σ4–Diamino–2–oxo–1 (2H)–pyrimidinehexanoic Acid", J. Org. Chem. 56: 6007–6018 (1991).

Inaki, Y. and Takemoto, K. "Functionality and Applicability of Synthetic Nucleic Acid Analogs", In Current Topics in Polymer Science; Ottenbrite, Utracki, Inoue, Eds. Munich; New York: Hanser Publishers; New York : Distributed in the U.S.A. by Macmillan Pub. Co., 1, 80–100 (1987).

Inaki, Y. "Synthetic Nucleic Analogs", Prog. Polym. Sci. 17: 515–570 (1992).

Inoue et al., "Synthesis and properties of novel nucleic acid probes", Nuc Acids Res Symposiou Series 16: 165 (1985).

Inoue et al., "Synthesis and Hybridization Studies on Two complementary NONa (2'–O–methyl) ribonucleotides" Nucleic Acids Res 15: 6131–6148 (1987).

Inoue et al., "Sequence–dependent hydrolysis of RNA using modified Oligonucleotide Splints and R Nase H.," FEBS Ltrs. 215: 327–330 (1987).

Kahn et al., "The c–K–ras Gene and Human Cancer" (Review) *Anticancer Res* 7: 639–652 (1987).

Kawasaki et al., "Uniformly modified 2'–Deoxy–2'–fluoro Phosphorothioate Oligonucleotides as nuclease–Resistant Antisense Compounds with High Affinity and Specificity for RNA Targets," J.Med. Chem. 36 831–841 (1993).

Kawasaki et al., "Synthesis and Biophysical Studies of 2'–dR1B0–2'–F Modifed Oligonucleotides", 1–9 disclosed (1991).

Lal et al., "Diphenylphosphoryl Azide A Novel Reagent for the Stereospecific Synthesis of Azides from Alcohols," *Tetrahedron Letters* 23 1977–1980 (1977).

Lima et al., "Implication of RNA Structure on Antisense Oligonucleotide Hybridization Kinetics", *Biochemistry* 31: 12055–12061 (1991).

Lu, C.X., et. al. "Synthesis of Polyesters Containing Nucleic Acid Base Derivatives as Pending Side Chains":, J. Polym. Sci.: Part A:Polymer Chemistry 24: 525–36 (1986).

McCurdy et al., "Deoxyoligonucleotides with Inverted Polarity: Synthesis and Use in Triple–Helix Formation," *Nucleosides and Nucleotides* 10: 287–290 (1991).

Miller and Ts'o, "A new approach to chemotherapy based on molecular biology and nucleic acid chemistry: Matagen (masking tape for gene expression)" Antic–Cancer Drug Design 2: 117–128 (1987).

Miller et al., "Annual Reports in Medicinal Chemistry 23, Chapter 30: Oligonucleotide Inhibitors of Gene Expression in Living Cells: New Opportunities in Drug Design", pp. 295–304 (1988).

Monia, et. al., "Evaluation of 2'–Modified Oligonucleotides Containing 2'–Deoxy Gaps as Antisense Inhibitors of Gene Expression", *J. Bio. Chem.* 268: 14514–14522 (1993).

Nagae, S., et. al. "Functional Monomers and Polymers. CLIV. Application of Nucleic Acid Base Containing Polymers to High Performance Liquid Chromatography":, J. Polym. Sci.: Part A:Polymer Chemistry 27: 2593–2609 (1989).

Nielsen et al., "Sequence–Selective Recognition of DNA by Strand Displacement with a Thymine–Substituted Polyamide." *Science*, 254:1497–1500, 1991.

Nollet, A.J.H., et. al. "Unconventional Nucleotide Analogues–III, 4–(N₁–Pyrimidyl)–2–Aminobutyric Acids", Tetrahedron 25: 5989–5994 (1986).

Nollet, A.J.H., et. al. "Unconventional Nucleotide Analogues–II Synthesis of the Adenyl Analogue of Willardiine", Tetrahedron 25: 5983–5987 (1969).

Nollet, A.J.H., et. al. "Unconventional Nucleotide Analogues–I, $N_9$–Purinyl α–Amino Acids", Tetrahedron 25: 5971–5981 (1969).

Nollet, A.J.H., et. al. "Michael Addition of 4–O–Ethyluracil. A Method for Specific $N_1$–Alkylation of Hydroxypyrimidines", Tetrahedron Letters 53: 4605–4606 (1969).

Oligonucleotides: Antisense Inhibitors of Gene Expression, CRC Press, Inc., Boca Raton, Fl (1989).

Owen et al., "Transcriptional Activation of a Conserved Sequence Element by RAS Requires a Nuclear Factor Distinct from C–fos or C–jun", *Proc. Natl. Acad. Sci. U.S.A.* 1990, 87, 3866–3870.

Petersen et al., "Chemical Synthesis of Dimer Ribonucleotides Containing Internucleotidic Phosphoradithioate Linkages", Tetrahedron Letters 31: 911–914 (1990).

Petersheim and Turner, "Base–Stacking and Base–Pairing Contributions to Helix Stability Thermodynamics of Double–Helix Formation with CCGG, CCGGp, CCGGAp, ACCGGp, CCGGUp, and ACCGGUp", *Biochemistry* 22: 256–263 (1983).

Pitha, P.M., et. al. "Inhibition of Murine Leukemia Virus Replication by Poly(vinyluracil) and Poly(vinyladenine)", Proc. Natl. Acad. Sci. USA 70: 1204–1208 (1973).

Pitha, J. "Physiological Activities of Synthethic Analogs of Polynucleotides", Adv. Polym. Sci. 50: 1–16 (1983).

Puglisi and Tinoco, "Absorbance Melting Curves of RNA", *Methods in Enzymol.* 180: 304–325 (1989).

Reddy, P.E. et al., "A Point Mutation is Responsible for the Acquisition of Transforming Properties by the T24 Human Bladder Carcinoma Oncogene", *Nature* 300: 149–152 (1982).

Sagi et. al., "Base-Modified Oligodeoxynucleotides. I. Effect of 5-Alkyl, 5-(1-Alkenyl) and 5-(1-Alkynyl) Substitution of teh Pyrimidines on Duplex Stability and Hydrophobicity." *Tetrahedron Letters*, 34:2191–2194, (1993).

Saison–Behmoaras et al., "Short Modified Anti-sense Oligonucleotides Directed Against Ha-ras Point Mutation Induce Selective Cleavage of the mRNA and Inhibit T24 Cells Proliferation", EMBO Journal 10: 1111–1118 (1991).

Simon, R.J., et. al. "Peptoids: A modular approach to drug discovery", Proc. Natl. Acad. Sci. USA 89: 9367–9371 (1992).

Spalholtz et al., "Bovine papillomavirus Transcriptional Regulation: Localization of the E2-Responsive Elements of the Long Control Region," *J. Virol.* 61: 2128–2137 (1987).

Stawinski Jacek, et al., *Tenth International Roundtable: Nucleosides, Nucleotides and Their Biological Evaluation*, Sep. 16–20, 1992, Abstracts of Papers, Abstract 80.

Stenberg et. al., "Promoter-Specific trans Activation and Repression by Human Cytomegalovirus Immediate-Early Proteins Involves Common and Unique Protein Domains," *J. Virol.* 64: 1556–1565 (1990).

Tabin, C.J. et al., "Mechanism of Activation of a Human Oncogene", *Nature* 300: 143–149 (1982).

Takemoto, K., et. al. "Synthetic Nucleic Acid Analogs. Preparation and Interactions", Adv. Polym. Sci. 41: 1–51 (1981).

Taparowsky, E. et al., "Activation of the T24 Bladder Carcinoma Transforming Gene is Linked to a Single Amino Acid Change", *Nature* 300: 762–765 (1982).

Tibanyenda et al., "The effect of single base-pair mismatches on the duplex stability of d(T-A-T-T-A-A-T-A-T-C-A-A-G-T-T-G) . d(C-A-A-C-T-T-G-A-T-A-T-T-A-A-T-A)," *Eur. J. Biochem.*, 139:19–27, 1984.

Uhlmann, E., et. al. "Antisense Oligonucleotides: A New Therapeutic Principle", Chemical Reviews 90: 544–584 (1990).

Vasseur et al., "Oligonucleosides: Synthesis of a Novel Methylhydroxylamine-Linked Nucleoside Dimer and Its Incorporation into Antisense Sequences," *J. Am. Chem. Soc.*, 114: 4006–4007 (1992).

Vickers et al., "Inhibition of HIV-LTR gene expression by oligonucleotides targeted to the TAR element," *Nucleic Acids Research* 19: 3359–3368 (1991).

Weller, D.D., et. al. "Molecular Modeling of Acyclic Polyimide Oligonucleotide Analogues", J. Org. Chem. 6000–6006 (1991).

Gura, T. 1995, Science 270, 575–577.

Stein et al. 1993, Science 261: 1004–1012.

Wagner, R. W., 1994 Nature 372: 333–335.

Stull et al. 1995, Pharmaceutical Res. 12(4): 465–483.

Ikehara et al. 1977 Nuc. Acids. Res. 4(12): 4249–4260.

Koziolkiewicz et al. 1986 Chemica Scripta 26: 251–260.

Agrawal et al. 1987 Tetrahedron Letters 28(31): 3539–3542.

PNA-DNA-PNA CHIMERIC MACROMOLECULES

CROSS REFERENCE TO RELATED APPLICATIONS

This application is a continuation-in-part of my prior application Ser. No. PCT/US92/11339, filed Dec. 23, 1992, entitled "Gapped 2' Modified Oligonucleotides", that in turn is a continuation-in-part to my prior applications Ser. No. 814,961, filed Dec. 24, 1991, entitled "Gapped 2' Modified Oligonucleotides," now abandoned both of which are commonly assigned with this application. This application is further related to application Ser. No. 088,658, filed Jul. 2, 1993, entitled "Higher Order Structure and Binding of Peptide Nucleic Acids, commonly assigned in part with this application. That application is a continuation-in-part of application Ser. No. 054,363, filed Apr. 26, 1993, entitled "Novel Peptide Nucleic Acids," which in turn is a continuation-in-part of application PCT EP/91/01219, filed May 19, 1992. The disclosures of each of these applications are herein incorporated by reference.

FIELD OF THE INVENTION

This invention is directed to the synthesis and use of chimeric molecules having a PNA-DNA-PNA structure wherein each "PNA" is a peptide nucleic acid and the "DNA" is a phosphodiester, phosphorothioate or phosphorodithioate 2'-deoxyoligonucleotide. In a cell, a cellular extract or a RNase H containing diagnostic test system, a chimeric macromolecule of the invention having a base sequence that is hybridizable to a RNA target molecule can bind to that target RNA molecule and elicit a RNase H strand cleavage of that RNA target molecule.

BACKGROUND OF THE INVENTION

It is well known that most of the bodily states in mammals including most disease states, are effected by proteins. Such proteins, either acting directly or through their enzymatic functions, contribute in major proportion to many diseases in animals and man. Classical therapeutics has generally focused upon interactions with such proteins in an effort to moderate their disease causing or disease potentiating functions. Recently, however, attempts have been made to moderate the actual production of such proteins by interactions with messenger RNA (mRNA) or other intracellular RNA's that direct protein synthesis. It is generally the object of such therapeutic approaches to interfere with or otherwise modulate gene expression leading to undesired protein formation.

Antisense methodology is the complementary hybridization of relatively short oligonucleotides to single-stranded RNA or single-stranded DNA such that the normal, essential functions of these intracellular nucleic acids are disrupted. Hybridization is the sequence specific hydrogen bonding via Watson-Crick base pairs of the heterocyclic bases of oligonucleotides to RNA or DNA. Such base pairs are said to be complementary to one another.

Naturally occurring events that provide for the disruption of the nucleic acid function, as discussed by Cohen in *Oligonucleotides: Antisense Inhibitors of Gene Expression*, CRC Press, Inc., Boca Raton, Fla. (1989) are thought to be of at least two types. The first is hybridization arrest. This denotes the terminating event in which an oligonucleotide inhibitor binds to a target nucleic acid and thus prevents, by simple steric hindrance, the binding of essential proteins, most often ribosomes, to the nucleic acid. Methyl phosphonate oligonucleotides (see, e.g., Miller, et al., *Anti-Cancer Drug Design* 1987, 2, 117) and α-anomer oligonucleotides are the two most extensively studied antisense agents that are thought to disrupt nucleic acid function by hybridization arrest.

In determining the extent of hybridization arrest of an oligonucleotide, the relative ability of an oligonucleotide to bind to complementary nucleic acids may be compared by determining the melting temperature of a particular hybridization complex. The melting temperature ($T_m$), a characteristic physical property of double helixes, denotes the temperature in degrees centigrade at which 50% helical (hybridized) versus coil (unhybridized) forms are present. $T_m$ is measured by using the UV spectrum to determine the formation and breakdown (melting) of hybridization. Base stacking which occurs during hybridization, is accompanied by a reduction in UV absorption (hypochromicity). Consequently a reduction in UV absorption indicates a higher $T_m$. The higher the $T_m$, the greater the strength of the binding of the strands. Non-Watson-Crick base pairing, i.e. base mismatch, has a strong destabilizing effect on the $T_m$.

The second type of terminating event for antisense oligonucleotides involves the enzymatic cleavage of the targeted RNA by intracellular RNase H. The mechanism of such RNase H cleavages requires that a 2'-deoxyribofuranosyl oligonucleotide hybridize to a targeted RNA. The resulting DNA-RNA duplex activates the RNase H enzyme; the activated enzyme cleaves the RNA strand. Cleavage of the RNA strand destroys the normal function of the RNA. Phosphorothioate oligonucleotides are one prominent example of antisense agents that operate by this type of terminating event. For a DNA oligonucleotide to be useful for activation of RNase H, the oligonucleotide must be reasonably stable to nucleases in order to survive in a cell for a time sufficient for the RNase H activation.

Several recent publications of Walder, et al. further describe the interaction of RNase H and oligonucleotides. Of particular interest are: (1) Dagle, et al., *Nucleic Acids Research* 1990, 18, 4751; (2) Dagle, et al., *Antisense Research And Development* 1991, 1, 11; (3) Eder, et al., *J. Biol. Chem.* 1991, 266, 6472; and (4) Dagle, et al., *Nucleic Acids Research* 1991, 19, 1805. In these papers, Walder, et al. note that DNA oligonucleotides having both unmodified phosphodiester internucleoside linkages and modified, phosphorothioate internucleoside linkages are substrates for cellular RNase H. Since they are substrates, they activate the cleavage of target RNA by the RNase H. However, the authors further note that in Xenopus embryos, both phosphodiester linkages and phosphorothioate linkages are also subject to exonuclease degradation. Such nuclease degradation is detrimental since it rapidly depletes the oligonucleotide available for RNase H activation. As described in references (1), (2), and (4), to stabilize their oligonucleotides against nuclease degradation while still providing for RNase H activation, Walder, et al. constructed 2'-deoxy oligonucleotides having a short section of phosphodiester linked nucleotides positioned between sections of phosphoramidate, alkyl phosphonate or phosphotriester linkages. While the phosphoramidate containing oligonucleotides were stabilized against exonucleases, in reference (4) the authors noted that each phosphoramidate linkage resulted in a loss of 1.6° C. in the measured $T_m$ value of the phosphoramidate containing oligonucleotides. Such decrease in the $T_m$ value is indicative of an undesirable decrease in the hybridization between the oligonucleotide and its target strand.

Other authors have commented on the effect such a loss of hybridization between an antisense oligonucleotide and its targeted strand can have. Saison-Behmoaras, et al., *EMBO Journal* 1991, 10, 1111, observed that even through an oligonucleotide could be a substrate for RNase H, cleavage efficiency by RNase H was low because of weak hybridization to the mRNA. The authors also noted that the inclusion of an acridine substitution at the 3' end of the oligonucleotide protected the oligonucleotide from exonucleases.

U.S. Pat. No. 5,149,797 to Pederson et. al., that issued on Sep. 22, 1992 describes further oligonucleotides that operate by a RNase H mechanism. The oligonucleotides as claimed in this patent consist of an internal segment composed of phosphorothioate nucleotides flanked by methyl phosphonate, phosphoromorpholidates, phosphoropiperazidates or phosphoramidates. Since all of the components of these oligonucleotides, i.e. phosphorothioate, methyl phosphonates, phosphoromorpholidates, phosphoropiperazidates or phosphoramidates when used as oligonucleotide linkages individually decrease the hybridization between the oligonucleotide and its target strand, the comments of Saison-Behmoaras et al., could be equally applicable to the oligonucleotides described in this patent.

While it has been recognized that cleavage of a target RNA strand using an antisense oligonucleotide and RNase H would be useful, nuclease resistance of the oligonucleotide and fidelity of the hybridization are also of great importance. Heretofore, there have been no suggestion in the art of methods or materials that could both activate RNase H while concurrently maintaining or improving hybridization properties and providing nuclease resistance even though there has been a long felt need for such methods and materials. Accordingly, there remains a long-felt need for such methods and materials.

OBJECTS OF THE INVENTION

It is an object of this invention to provide chimeric macromolecules that hybridize with a target strand with improved binding affinity.

It is a further object to provide chimeric macromolecules that have stability against nuclease degradation.

A still further object is to provide chimeric macromolecules that activate RNase H for target strand cleavage.

A still further object is to provide research and diagnostic methods and materials for assaying cellular states in vitro and bodily states, especially diseased states, in animals.

Another object is to provide therapeutic and research methods and materials for the treatment of diseases through modulation of the activity of a target RNA.

BRIEF DESCRIPTION OF THE INVENTION

In accordance with this invention there are provided macromolecules formed from peptide nucleic acids and 2'-deoxyoligonucleotides. Such macromolecules have the structure: PNA-DNA-PNA, wherein the PNA portions are peptide nucleic acid sequences and the DNA portion is a phosphodiester, phosphorotioate or phosphorodithioate 2'-deoxyoligonucleotide sequence. The PNA portions of the macromolecule are believed to provide increased nuclease resistance and increased binding affinity of the macromolecule to target RNAs. The 2'-deoxyoligonucleotide portion is believed to elicit a RNase H response and cleavage of a RNA target strand.

The 2'-deoxyoligonucleotide, i.e. DNA, portions of the macromolecules of the invention are oligonucleotide segments formed from nucleotide units that have 2'-deoxy-erythro-pentofuranosyl sugar moieties. Each nucleotide includes a nucleobase attached to a 2'-deoxy-erythro-pentofuranosyl sugar moiety of the nucleotide. The nucleotides are linked together and/or to other moieties by phosphodiester linkages, phosphorothioate linkages and/or phosphorodithioate linkages. In certain preferred macromolecules of the invention each of the nucleotides of the 2'-deoxyoligonucleotide portion of the macromolecule are linked together by phosphorothioate linkages. In other preferred embodiments, the nucleotides of the 2'-deoxyoligonucleotide portion are linked together by phosphodiester linkages and in even further preferred embodiments, a mixture of phosphodiester and phosphorothioate linkages link the nucleotide units of the 2'-deoxyoligonucleotide together.

The peptide nucleic acid portions of the macromolecules increase the binding affinity of the macromolecule to a complementary strand of nucleic acid. It further provides for nuclease stability of the macromolecule against degradation by cellular nucleases. Selecting the 2'-deoxyoligonucleotide portion of the macromolecule to include one or more or all phosphorothioate or phosphorodithioate linkages provides further nuclease stability to the macromolecules of the invention.

The PNA portions of the macromolecules of the invention are made up of units comprising a N-(2-aminoethyl)glycine or analogues thereof having a nucleobase attached thereto via a linker such as a carboxymethyl moiety or analogues thereof to the nitrogen atom of the glycine portion of the unit. The units are coupled together via amide bonds formed between the carboxyl group of the glycine moiety and the amine group of the aminoethyl moiety. The nucleobase can be one of the four common nucleobases of nucleic acids or they can include other natural or synthetic nucleobases.

In preferred macromolecules of the invention the PNA-DNA-PNA structure is formed by connecting together the respective N-(2-aminoethyl)glycine PNA units and the respective 2'-deoxy-erythro-pentofuranosyl sugar phosphate DNA units. Thus the nucleobases of the PNA portion of the macromolecules of the invention are carried on a backbone composed of N-(2-aminoethyl)glycine PNA units and the nucleobases of the DNA portion of the macromolecules of the invention are carried on a backbone composed of 2'-deoxy-erythro-pentofuranosyl sugar phosphate units. Together the nucleobases of the PNA portions and the nucleobases of the DNA portion of the macromolecules of the invention are connected by their respective backbone units in a sequence that is hybridizable to a complementary nucleic acid, as for instance, a targeted RNA stand.

In preferred macromolecules of the invention the PNA and the DNA portions are joined together with amide linkages. In such preferred macromolecule of the invention the macromolecule is of the structure:

PNA-(amide link)-DNA-(amide link)-PNA.

Other linkages that can be used to join the PNA and the DNA portions include amine linkages and ester linkages.

The macromolecules of the invention preferably comprise from about 9 to about 30 total nucleobase bearing subunits. It is more preferred that the macromolecules comprise from about 15 to about 25 nucleobase bearing subunits. In order to elicit a RNase H response, as specified above, within this total overall sequence length of the macromolecule will be a sub-sequence of greater than 3 but preferably five or more consecutive 2'-deoxy-erythro-pentofuranosyl containing nucleotide subunits.

Preferred nucleobases of the invention for both the peptide nucleic acid and the 2'-deoxynucleotide subunits include adenine, guanine, cytosine, uracil, thymine, xanthine, hypoxanthine, 2-aminoadenine, 6-methyl and other alkyl adenines, 2-propyl and other alkyl adenines, 5-halo uracil, 5-halo cytosine, 5-propynyl uracil, 5-propynyl cytosine, 7-deazaadenine, 7-deazaguanine, 7-deaza-7-methyl-adenine, 7-deaza-7-methyl-guanine, 7-deaza-7-propynyl-adenine, 7-deaza-7-propynyl-guanine and other 7-deaza-7-alkyl or 7-aryl purines, N2-alkyl-guanine, N2-alkyl-2-amino-adenine, purine 6-aza uracil, 6-aza cytosine and 6-aza thymine, 5-uracil (pseudo uracil), 4-thiouracil, 8-halo adenine, 8-amino-adenine, 8-thiol adenine, 8-thiolalkyl adenines, 8-hydroxyl adenine and other 8 substituted adenines and 8-halo guanines, 8-amino guanine, 8-thiol guanine, 8-thiolalkyl guanines, 8-hydroxyl guanine and other 8 substituted guanines, other aza and deaza uracils, other aza and deaza thymidines, other aza and deaza cytosine, aza and deaza adenines, aza and deaza guanines or 5-trifluoromethyl uracil and 5-trifluorocytosine.

The invention also provides methods of treating an organism having a disease characterized by the undesired production of a protein. These methods include contacting the organism with a macromolecule having a sequence of nucleobases capable of specifically hybridizing to a complementary strand of nucleic acid. The methods further include having a portion of the nucleobases comprise peptide nucleic acid subunits (PNA units) and the remainder of the nucleobases comprise 2'-deoxynucleotide subunits (DNA units). The peptide nucleic acid subunits and the deoxynucleotide subunits are joined together to form a macromolecule of the structure PNA-DNA-PNA where the PNAs are peptide nucleic acids and DNA is an 2'-deoxyoligonucleotide.

Further in accordance with this invention there are provided compositions including a pharmaceutically effective amount of a macromolecule having a sequence of nucleobases capable of specifically hybridizing to a complementary strand of nucleic acid. A portion of the nucleobases comprise peptide nucleic acid subunits (PNA units) and the remainder of the nucleobases comprise 2'-deoxynucleotide nucleotide subunits (DNA units). The peptide nucleic acid subunits (the PNAs) and the deoxynucleotides subunits (the DNA) are joined together to form a macromolecule of the structure PNA-DNA-PNA. The compositions further include a pharmaceutically acceptable diluent or carrier.

Further in accordance with this invention there are provided methods for in vitro modification of a sequence specific nucleic acid including contacting a test solution containing an RNase H enzyme and said nucleic acid with a PNA-DNA-PNA macromolecule, as defined above.

There are also provided methods of concurrently enhancing hybridization and RNase H enzyme activation in an organism that includes contacting the organism with a PNA-DNA-PNA macromolecule, as defined above.

DETAILED DESCRIPTION OF THE INVENTION

Figure 1:
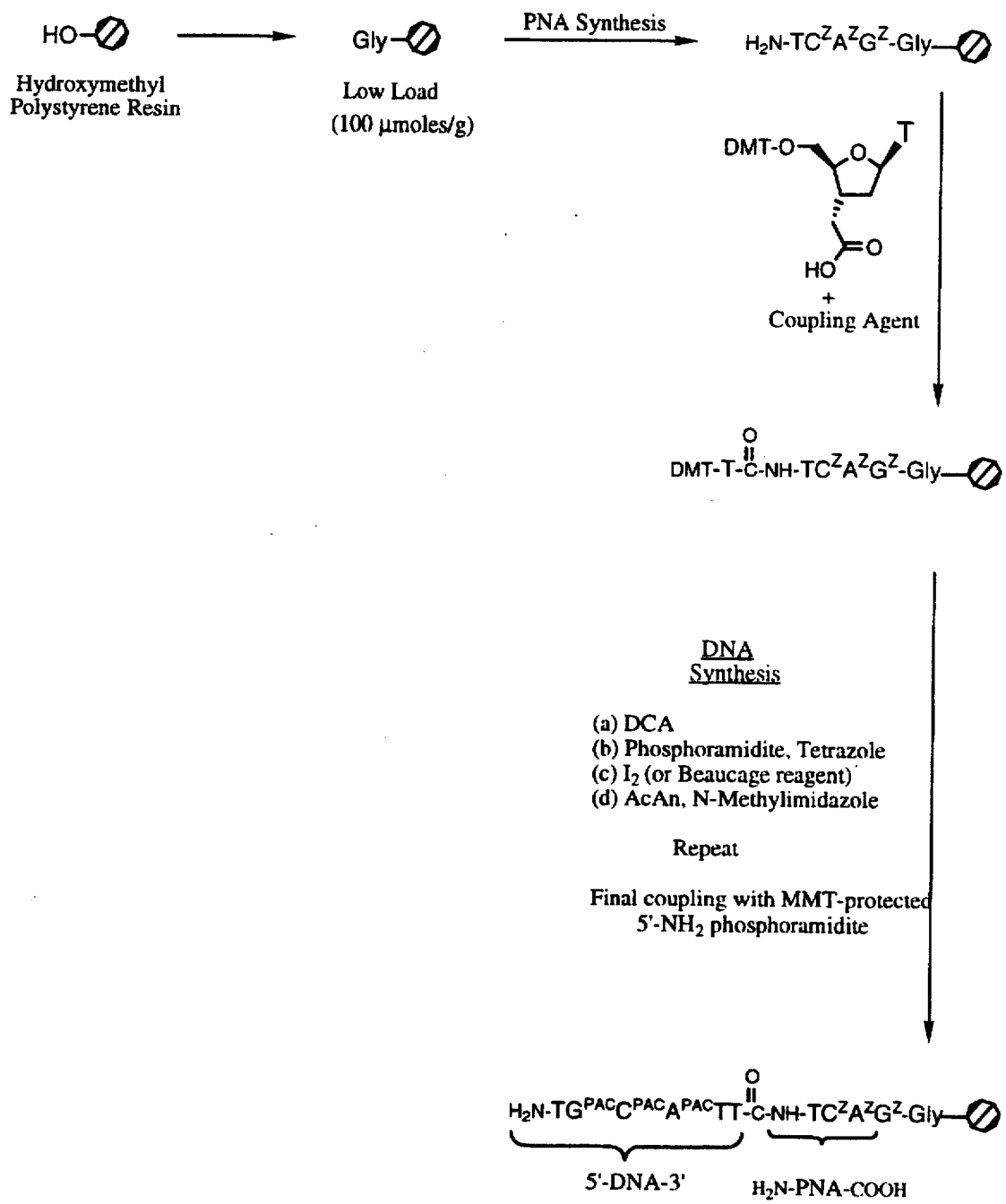
FIG. 1 is a chemical schematic illustrating solid phase synthesis of certain compounds of the invention.

In accordance with the objects of this invention, novel macromolecules are provided that, at once, have increased nuclease resistance, increased binding affinity to complementary strands and that are substrates for RNase H. The macromolecules of the invention are assembled from a plurality of peptide nucleic acid subunits (PNA subunits) and a plurality of 2'-deoxynucleotide subunits (DNA subunits). They are assembled into a macromolecule of the structure: PNA-DNA-PNA. Each peptide nucleic acid subunit and each 2'-deoxynucleotide subunit includes a nucleobase that is capable of specifically hybridizing with like nucleobases on a target RNA molecules or other target molecules including DNA molecules and proteins.

The peptide nucleic acid portions of the macromolecules of the invention bestow increased nuclease resistance to the macromolecules of the invention. Further, these same peptide nucleic acid portions bestow increased binding affinity of the macromolecules of the invention to a complementary strand of nucleic acid. The 2'-deoxynucleotide portion of the macromolecules of the invention each include a 2'-deoxy-erythro-pentofuranosyl group as their sugar moiety.

In conjunction with the above guidelines, each of the 2'-deoxynucleotide subunits can be a "natural" or a "synthetic" moiety. Thus, in the context of this invention, the term "oligonucleotide" in a first instance refers to a polynucleotide formed from a plurality of joined nucleotide units. The nucleotides units are joined together via native internucleoside, phosphodiester linkages. The nucleotide units are formed from naturally-occurring bases and 2'-deoxy-erythro-pentofuranosyl sugars groups. The term "oligonucleotide" thus effectively includes naturally occurring species or synthetic species formed from naturally occurring nucleotide units.

The term oligonucleotide is intended to include naturally occurring structures as well as non-naturally occurring or "modified" structures—including modified base moieties that function similarly to natural bases. The nucleotides of the 2'-deoxyoligonucleotide portion of the macromolecule can be joined together with other selected synthetic linkages in addition to the natural phosphodiester linkage. These other linkages include phosphorothioate and phosphorodithioate inter-sugar linkages. Further suggested as suitable linkages are phosphoroselenate and phosphorodiselenate linkages. The base portion, i.e., the nucleobase of the 2'-deoxynucleotides, can include the natural bases, i.e. adenine, guanine, cytosine, uracil or thymidine. Alternately they can include deaza or aza purines and pyrimidines used in place of natural purine and pyrimidine bases; pyrimidine bases having substituent groups at the 5 or 6 position; purine bases having altered or replacement substituent groups at the 2, 6 or 8 positions. They may also comprise other modifications consistent with the spirit of this invention. Such 2'-deoxyoligonucleotides are best described as being functionally interchangeable with natural oligonucleotides (or synthesized oligonucleotides along natural lines), but which have one or more differences from natural structure. All such 2'-deoxyoligonucleotides are comprehended by this invention so long as they function effectively in the macromolecule to elicit the RNase H cleavage of a target RNA strand.

In one preferred embodiment of this invention, nuclease resistance beyond that confirmed by the peptide nucleic acid portion of the macromolecule is achieved by utilizing phosphorothioate internucleoside linkages. Contrary to the reports of Walder, et al. note above, I have found that in systems such as fetal calf serum containing a variety of 3'-exonucleases, modification of the internucleoside linkage from a phosphodiester linkage to a phosphorothioate linkage provides nuclease resistance.

Brill, et al., *J. Am. Chem. Soc.* 1991, 113, 3972, recently reported that phosphorodithioate oligonucleotides also exhibit nuclease resistance. These authors also reported that phosphorodithioate oligonucleotide bind with complementary deoxyoligonucleotides, stimulate RNase H and stimulate the binding of lac repressor and cro repressor. In view of these properties, phosphorodithioates linkages also may be use in the 2'-deoxyoligonucleotide portion of the macromolecules of the invention. The synthesis of phosphorodithioates is further described by Beaton, et. al., Chapter 5, Synthesis of oligonucleotide phosphorodithioates, page 109, *Oligonucleotides and Analogs*, A Practical Approach, Eckstein, F., Ed.; The Practical Approach Series, IRL Press, New York, 1991.

When increased nuclease resistance is conferred upon a macromolecule of the invention by the use of a phosphorothioate or phosphorodithioates internucleotide linkages, such linkages will reside in each internucleotide site. In other embodiments, less than all of the internucleotide linkages will be modified to phosphorothioate or phosphorodithioate linkages.

I have found that binding affinity of macromolecules of the invention is increased by virtue of the peptide nucleic acid portions of the macromolecules. As for example the $T_m$ of a 10 mer homothymidine PNA binding to its complementary 10 mer homoadenosine DNA is 73° C. whereas the $T_m$ for the corresponding 10 mer homothymidine DNA to the same complementary 10 homoadenosine DNA is only 23° C.

Binding affinity also can be increased by the use of certain modified bases in both the nucleotide subunits that make up the 2'-deoxyoligonucleotides of the invention and in the peptide nucleic acid subunits. Such modified bases may include 5-propynylpyrimidines, 6-azapyrimidines, and N-2, N-6 and O-6 substituted purines including 2-aminopropyladenine. Other modified pyrimidine and purine base are also expected to increase the binding affinity of macromolecules to a complementary strand of nucleic acid.

For use in preparing such structural units, suitable nucleobases include adenine, guanine, cytosine, uracil, thymine, xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thiolalkyl, hydroxyl and other 8 substituted adenines and guanines, 5-trifluoromethyl and other 5 substituted uracils and cytosines, 7-methylguanine and other nucleobase such as those disclosed in U.S. Pat. No. 3,687,808, those disclosed in the *Concise Encyclopedia Of Polymer Science And Engineering*, J. I. Kroschwitz, Ed. John Wiley & Sons, 1990 at pages 858–859 and those disclosed by Englisch, U. and Gauss, D. H., *Angewandte Chemie, International Edition* 1991, 30, 613 are selected.

In order to elicit RNase H enzyme cleavage of a target RNA, a macromolecule of the invention must include a segment or sub-sequence therein that is a DNA type segment. Stated otherwise, at least a portion of the macromolecules of the invention must be nucleotide subunits having 2'-deoxy-erythro-pentofuranosyl sugar moieties. I have found that a sub-sequence having more than three consecutive, linked 2'-deoxy-erythro-pentofuranosyl-containing nucleotide subunits likely is necessary in order to elicit RNase H activity upon hybridization of a macromolecule of the invention with a target RNA. It is presently preferred to have a sub-sequence of 5 or more consecutive 2'-deoxy-erythro-pentofuranosyl containing nucleotide subunits in a macromolecule of the invention. Use of at least 7 consecutive 2'-deoxy-erythro-pentofuranosyl-containing nucleotide subunits is particularly preferred.

The overall length of the macromolecules of the invention can be from 3 to hundreds of subunits long; however, since target specificity can be achieved with a much shorter molecule, a more practical maximum length will be from about 30 to about 50 subunits long. An even more preferred maximum length will be about 25 subunits long.

Depending upon the target, the minimum length of the macromolecule will vary from three to about fifteen total subunits. It has been found in practice that in using antisense oligonucleotides generally a minimum length of about 15 nucleotides is necessary to insure proper affinity upon hybridization. However as noted above, since the peptide nucleic acid subunits have a greater hybridization affinity for target molecules compared to normal phosphodiester oligonucleotides that in turn have a better affinity than phosphorothioate oligonucleotides, in using the macromolecules of the invention, a minimum length less than that normally use in practicing antisense binding with antisense oligonucleotides can be expected. Taking these factors in to consideration a preferred length of the macromolecules will be from about 3 to about 30 total subunits with a more preferred range from about 9 to about 25 subunits in length.

In the macromolecules of the invention, there will be one or more sequential DNA units interspaced between PNA units. To elicit a RNase H response, as noted above preferably the DNA portion of the macromolecule will have at least three 2'-deoxynucleotide units. In determining an upper range of the number of DNA units, consideration is given to several factors including overall length of the macromolecule, the phosphate linkage utilized, desired fidelity to a target sequence and other like factors. Normally, for economic considerations it is desirable not to have more nucleobase units in the macromolecules of the invention than is necessary to bind with specificity to a target molecule and, if desired, to elicit an RNase H response. For utilization of the RNase H mechanism this number is generally about 5 nucleotides. Additionally since phosphorothioate and phosphorodithioate phosphate linkage themselves exhibit nuclease resistance, with use of these two phosphate linkages, a longer stretch of DNA subunits can be utilized compared to phosphodiester subunits that must rely on the PNA portions of the macromolecule for nuclease resistance. Taking these factors into account, a particularly preferred working range includes macromolecules of the invention is from 9 to about 28 subunits in length and having from about five to about eight of those subunits being sequential located 2'-deoxynucleotide subunits.

The mechanism of action of RNase H is recognition of a DNA-RNA duplex followed by cleavage of the RNA stand of this duplex. As noted in the Background section above, others in the art have used modified DNA strands to impart nuclease stability to the DNA strand. To do this they have used modified phosphate linkages that impart increased nuclease stability but concurrently detract from hybridization properties.

While I do not wish to be bound by theory in the macromolecules of the invention, I have recognized that by positioning peptide nucleic acid units at both ends of a 2'-deoxyolignucleotide portion of the macromolecule this will impart nuclease stability to the macromolecule. Further this will also impart increase binding and specificity to a complementary strand.

Again, while not wishing to be bound by any particular theory, I have recognized certain criteria that must be met for RNase H to recognize and elicit cleavage of a RNA strand. The first of these is that the RNA stand at the cleavage site must have its nucleosides connected via a phosphate linkage that bears a negative charge. Additionally, the sugar of the nucleosides at the cleavage site must be a β-pentofuranosyl sugar and also must be in a 2' endo conformation. The only nucleosides (nucleotides) that fit this criteria are phosphodiester, phosphorothioate, phosphorodithioate, phosphoroselenate and phosphorodiselenate nucleotides of 2'-deoxy-erythro-pentofuranosyl β-nucleosides.

In view of the above criteria, even certain nucleosides that have been shown to reside in a 2' endo conformation (e.g., cyclopentyl nucleosides) will not elicit RNase H activity since they do not incorporate a pentofuranosyl sugar. Modeling has shown that oligonucleotide 4'-thionucleosides also will not elicit RNase H activity, even though such nucleosides reside in an envelope conformation, since they do not reside in a 2' endo conformation. Additionally, since α-nucleosides are of the opposite configuration from β-pentofuranosyl sugars they also will not elicit RNase H activity.

Nucleobases that are attached to phosphate linkages via non-sugar tethering groups or via non-phosphate linkages also do not meet the criteria of having a β-pentofuranosyl sugar in a 2' endo conformation. Thus, they likely will not elicit RNase H activity.

For incorporation into the 2'-deoxyoligonucleotide portion of the macromolecule of the invention, nucleosides will be blocked in the 5' position with a dimethoxytrityl group, followed by phosphitylation in the 3' position as per the tritylation and phosphitylation procedures reported in *Oligonucleotides and Analogs, A Practical Approach*, Eckstein, F., Ed.; The Practical Approach Series, IRL Press, New York, 1991. Incorporation into oligonucleotides will be accomplished utilizing a DNA synthesizer such as an ABI 380 B model synthesizer using appropriate chemistry for the formation of phosphodiester, phosphorothioate or phosphorodithioate phosphate linkages as per the synthetic protocols illustrated in Eckstein op. cit.

The 2'-deoxynucleotide subunits and the peptide nucleic acid subunits of the macromolecules of the invention are joined by covalent bonds to fix the subunits of the macromolecule in the desired nucleobase sequence. A covalent interconnection of a desired length is formed between each of the two adjacent regions of the macromolecule. Preferably a covalent interconnection is achieved by selecting a linking moiety that can form a covalent bond to both of the different types of subunit moieties forming the adjacent regions. Preferably the linking moiety is selected such that the resulting chain of atoms between the linking moiety and the different types of moieties is of the same length. In one preferred embodiment of the invention, particularly useful as a linkage that interconnect the 2'-deoxynucleotide and peptide nucleic acid subunits are amide linkages. In other embodiments amine and ester linkages can be used.

The peptide nucleic acid subunit portions (the PNA portions) of the macromolecules of the invention have the general formula (I):

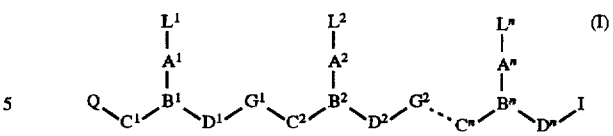

wherein:

n is at least 2, each of $L^1$—$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, and reporter ligands, at least one of $L^1$—$L^n$ being a naturally occurring nucleobase, a non-naturally occurring nucleobase, a DNA intercalator, or a nucleobase-binding group;

each of $R^3$ and $R^4$ is independently selected from the group consisting of hydrogen ($C_1$–$C_4$)alkyl, hydroxy- or alkoxy- or alkylthio-substituted ($C_1$–$C_4$)alkyl, hydroxy, alkoxy, alkylthio and amino;

each of $C^1$—$C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined above, and $R^5$ is hydrogen, ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;

each of $D^1$—$D^n$ is $(CR^6R^7)_z$ where $R^6$ and $R^7$ are as defined above;

each of y and z is zero or an integer from 1 to 10, the sum y+z being greater than 2 but not more than 10;

each of $G^1$—$G^{n-1}$ is —$NR^3CO$—, —$NR^3CS$—, —$NR^3SO$— or —$NR^3SO_2$—, in either orientation, where $R^3$ is as defined above;

each pair of $A^1$—$A^n$ and $B^1$—$B^n$ are selected such that:
 (a) A is a group of formula (IIa), (IIb) or (IIc) and B is N or $R^3N^+$; or
 (b) A is a group of formula (IId) and B is CH;

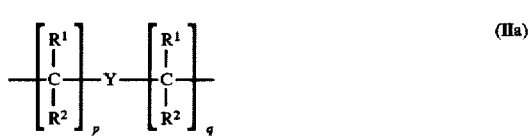

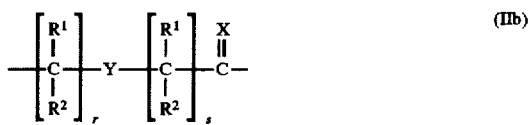

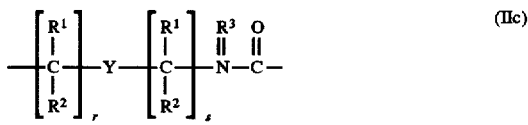

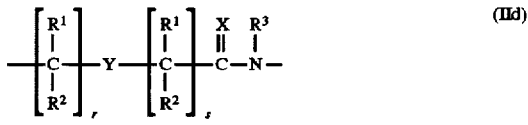

where:
X is O, S, Se, $NR^3$, $CH_2$ or $C(CH_3)_2$;

Y is a single bond, O, S or NR$^4$;

each of p and q is zero or an integer from 1 to 5, the sum p+q being not more than 10;

each of r and s is zero or an integer from 1 to 5, the sum r+s being not more than 10;

each R$^1$ and R$^2$ is independently selected from the group consisting of hydrogen, (C$_1$–C$_4$)alkyl which may be hydroxy- or alkoxy- or alkylthio-substituted, hydroxy, alkoxy, alkylthio, amino and halogen;

each of G$^1$—G$^{n-1}$ is —NR$^3$CO—, —NR$^3$CS—, —NR$^3$SO— or —NR$^3$SO$_2$—, in either orientation, where R$^3$ is as defined above;

Q is —C$_2$H, —CONR'R", —SO$_3$H or —SO$_2$NR'R" or an activated derivative of —CO$_2$H or —SO$_3$H; and I is —NHR'"R"" or —NR'"C(O)R"", where R', R", R'" and R"" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

Preferred peptide nucleic acids have general formula (IIIa)–(IIIc):

Particularly preferred are compounds having formula (IIIa)–(IIIc) wherein each L is independently selected from the group consisting of the nucleobases thymine (T), adenine (A), cytosine (C), guanine (G) and uracil (U), k and m are zero or 1, and n is an integer from 1 to 30, in particular from 4 to 20.

The peptide nucleic acid portions of the macromolecules of the invention are synthesized by procedures, either in solution or on a solid phase, generally following the procedures described in patent application PCT/EP/01219 that published on Nov. 26, 1992 as publication WO 92/20702 or U.S. patent application Ser. No. 08/088,658, filed Jul. 2, 1993 or by equivalent procedures. The contents of these patent applications are herein incorporated by reference.

The synthons used are monomer amino acids or their activated derivatives, protected by standard protecting groups. The PNAs also can be synthesized by using the corresponding diacids and diamines.

The novel monomer synthons according to the invention are selected from the group consisting of amino acids, diacids and diamines having general formulae:

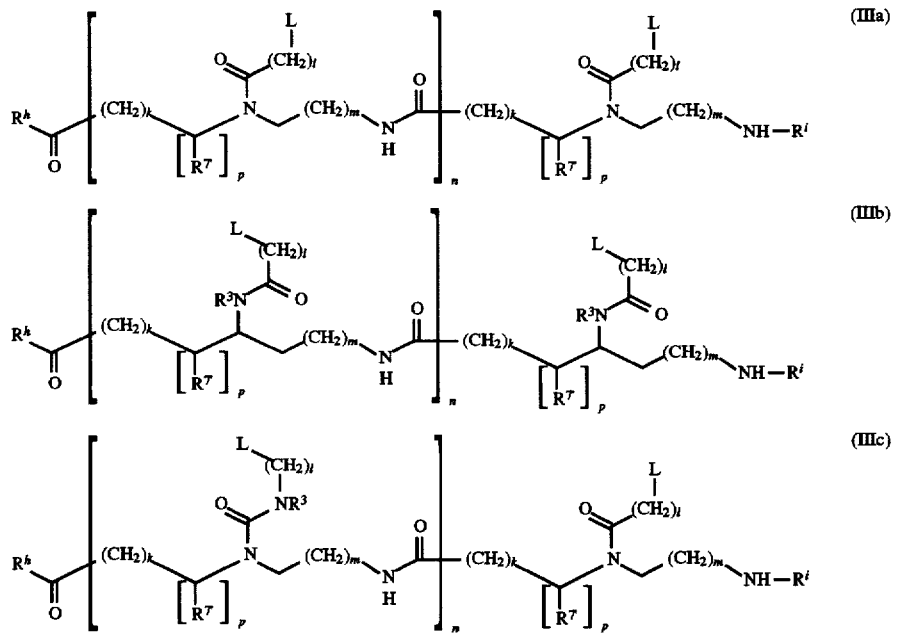

wherein:

each L ms independently selected from the group consisting of hydrogen, phenyl, heterocyclic moieties, naturally occurring nucleobases, and non-naturally occurring nucleobases;

each R$^{7'}$ is independently selected from the group consisting of hydrogen and the side chains of naturally occurring alpha amino acids;

n is an integer from 1 to 60;

each of k, l, and m is independently zero or an integer from 1 to 5;

p is zero or 1;

R$^h$ is OH, NH$_2$ or —NHLysNH$_2$; and

R$^i$ is H or COCH$_3$.

-continued

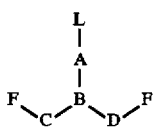
(VI)

wherein L, A, B, C and D are as defined above, except that any amino groups therein may be protected by amino protecting groups; E is COOH, CSOH, SOOH, SO$_2$OH or an activated derivative thereof; and F is NHR$^3$ or NPgR$^3$, where R$^3$ is as defined above and Pg is an amino protecting group.

Preferred monomer synthons according to the invention have formula (VIIIa)–(VIIIc):

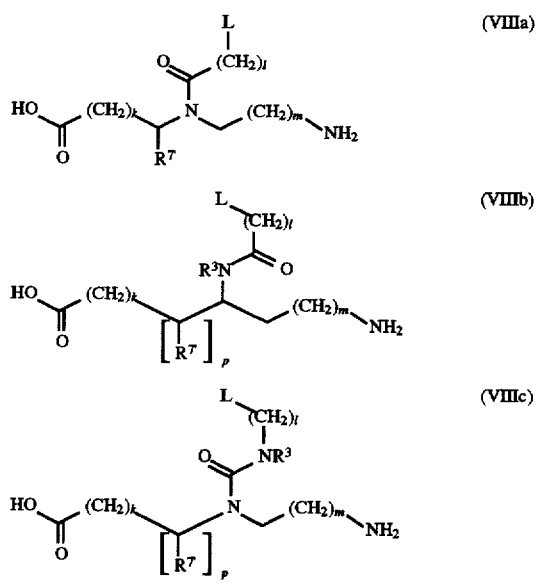

or amino-protected and/or acid terminal activated derivatives thereof, wherein L is selected from the group consisting of hydrogen, phenyl, heterocyclic moieties, naturally occurring nucleobases, and non-naturally occurring nucleobases; and R$^7$ is selected from the group consisting of hydrogen and the side chains of naturally occurring alpha amino acids.

Compounds of the invention can be utilized in diagnostics, therapeutics and as research reagents and kits. Further once identified as being active in a test system, they can be used as standards in testing systems for other active compounds including chemotherapeutic agents. They can be utilized in pharmaceutical compositions by including an effective amount of a macromolecule of the invention admixed with a suitable pharmaceutically acceptable diluent or carrier. They further can be used for treating organisms having a disease characterized by the undesired production of a protein. The organism can be contacted with a macromolecule of the invention having a sequence that is capable of specifically hybridizing with a strand of nucleic acid that codes for the undesirable protein.

Such therapeutic treatment can be practiced in a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to such therapeutic and/or prophylactic treatment. Seemingly diverse organisms such as bacteria, yeast, protozoa, algae, all plant and all higher animal forms, including warm-blooded animals, can be treated by this therapy. Further, since each of the cells of multi-cellular eukaryotes also includes both DNA-RNA transcription and RNA-protein translation as an integral part of their cellular activity, such therapeutics and/or diagnostics can also be practiced on such cellular populations. Furthermore, many of the organelles, e.g., mitochondria and chloroplasts, of eukaryotic cells also include transcription and translation mechanisms. As such, single cells, cellular populations or organelles also can be included within the definition of organisms that are capable of being treated with the therapeutic or diagnostic oligonucleotides of the invention. As used herein, therapeutics is meant to include both the eradication of a disease state, killing of an organism, e.g., bacterial, protozoan or other infection, or control of erratic or harmful cellular growth or expression.

For purpose of illustration, the compounds of the invention are used in a ras-luciferase fusion system using ras-luciferase transactivation. As described in U.S. patent application Ser. No. 07/715,196, filed Jun. 14, 1991, entitled Antisense Inhibition of RAS Oncogene and assigned commonly with this application, the entire contents of which are herein incorporated by reference, the ras oncogenes are members of a gene family that encode related proteins that are localized to the inner face of the plasma membrane. Ras proteins have been shown to be highly conserved at the amino acid level, to bind GTP with high affinity and specificity, and to possess GTPase activity. Although the cellular function of ras gene products is unknown, their biochemical properties, along with their significant sequence homology with a class of signal-transducing proteins known as GTP binding proteins, or G proteins, suggest that ras gene products play a fundamental role in basic cellular regulatory functions relating to the transduction of extracellular signals across plasma membranes.

Three ras genes, designated H-ras, K-ras, and N-ras, have been identified in the mammalian genome. Mammalian ras genes acquire transformation-inducing properties by single point mutations within their coding sequences. Mutations in naturally occurring ras oncogenes have been localized to codons 12, 13, and 61. The sequences of H-ras, K-ras and N-ras are known. Capon et al., Nature 302 1983, 33–37; Kahn et al., Anticancer Res. 1987, 7, 639–652; Hall and Brown, Nucleic Acids Res. 1985, 13, 5255–5268. The most commonly detected activating ras mutation found in human tumors is in codon 12 of the H-ras gene in which a base change from GGC to GTC results in a glycine-to-valine substitution in the GTPase regulatory domain of the ras protein product. Tabin, C. J. et al., Nature 1982, 300, 143–149; Reddy, P. E. et al., Nature 1982, 300, 149–152; Taparowsky, E. et al., Nature 1982, 300, 762–765. This single amino acid change is thought to abolish normal control of ras protein function, thereby converting a normally regulated cell protein to one that is continuously active. It is believed that such deregulation of normal ras protein function is responsible for the transformation from normal to malignant growth. Monia, et. al., J. Bio. Chem., 1993, 268, 14514–14522, have recently shown, via a transactivation reporter gene system, that chimeric "Gap" (structure having a 2'-deoxyoligonucleotide flanked by non-deoxyoligonucleotides) are active in vitro against the Ha-ras oncogene. Compounds of the invention active in the above described assays can be used as standards in in vitro chemotherapeutic agent test screens.

Figure 2:
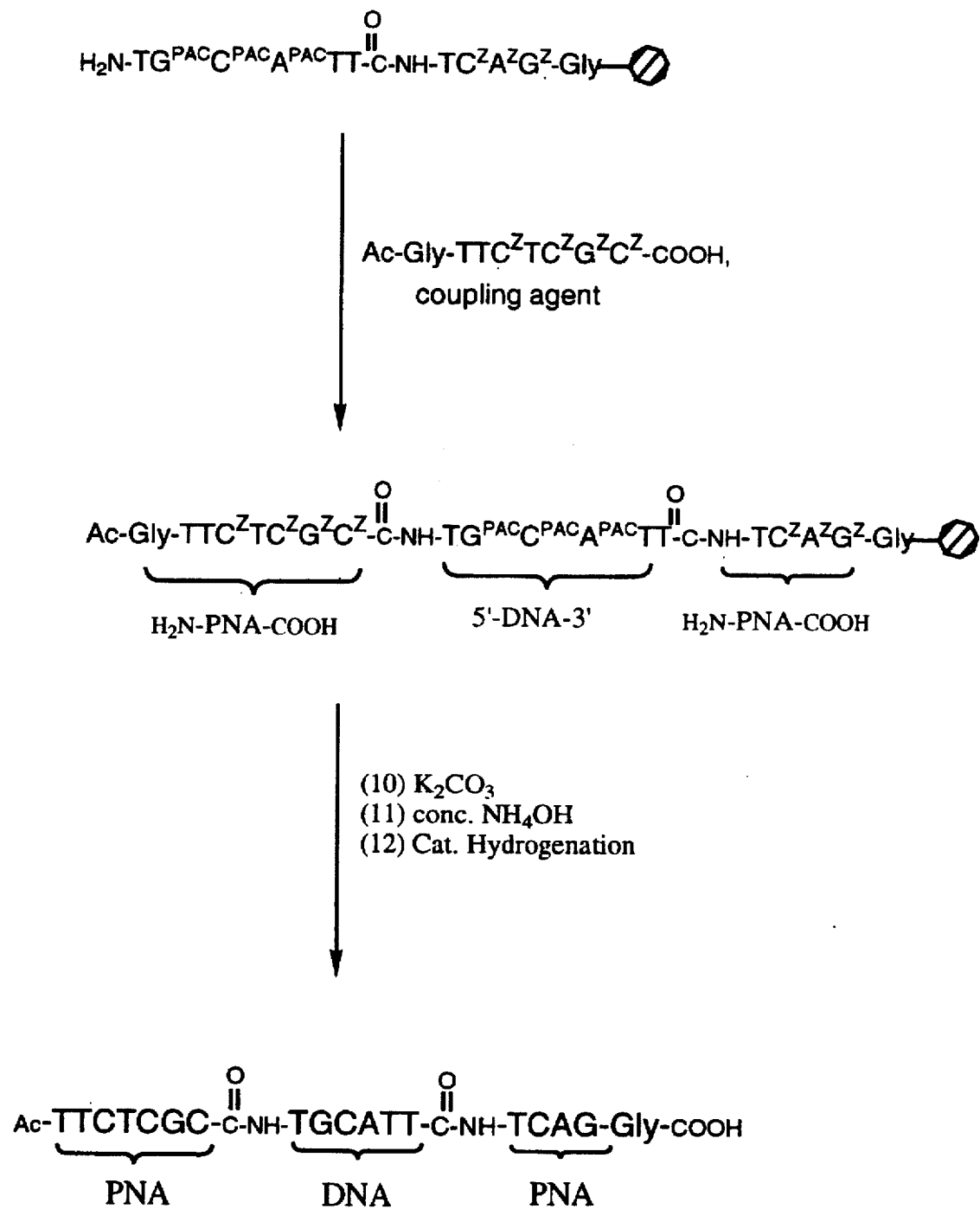
FIG. 2 is a chemical schematic illustrating solid phase synthesis of certain compounds of the invention.
Figure 3:
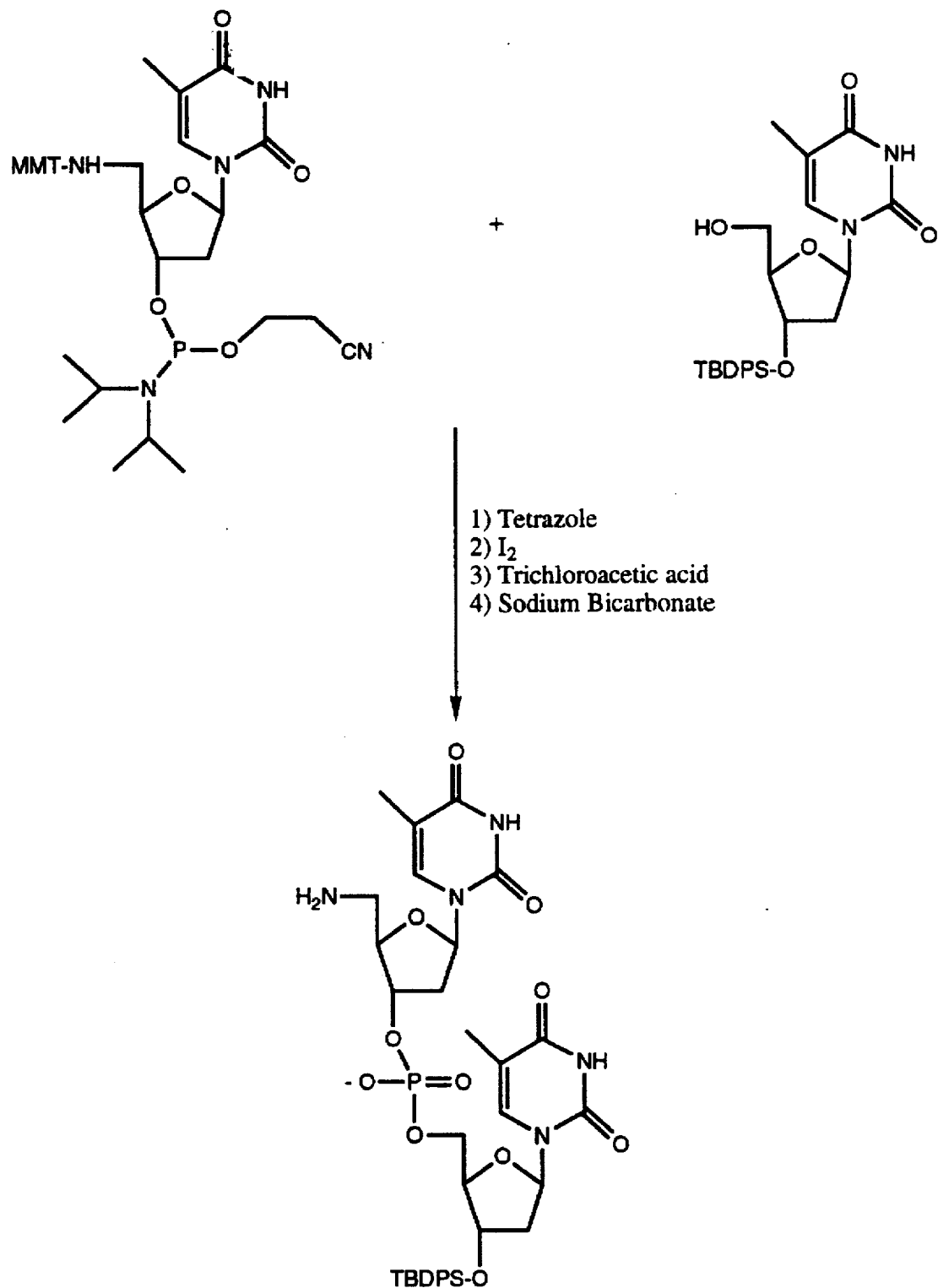
FIG. 3 is a chemical schematic illustrating solution phase synthesis of certain compounds of the invention.
Figure 4:
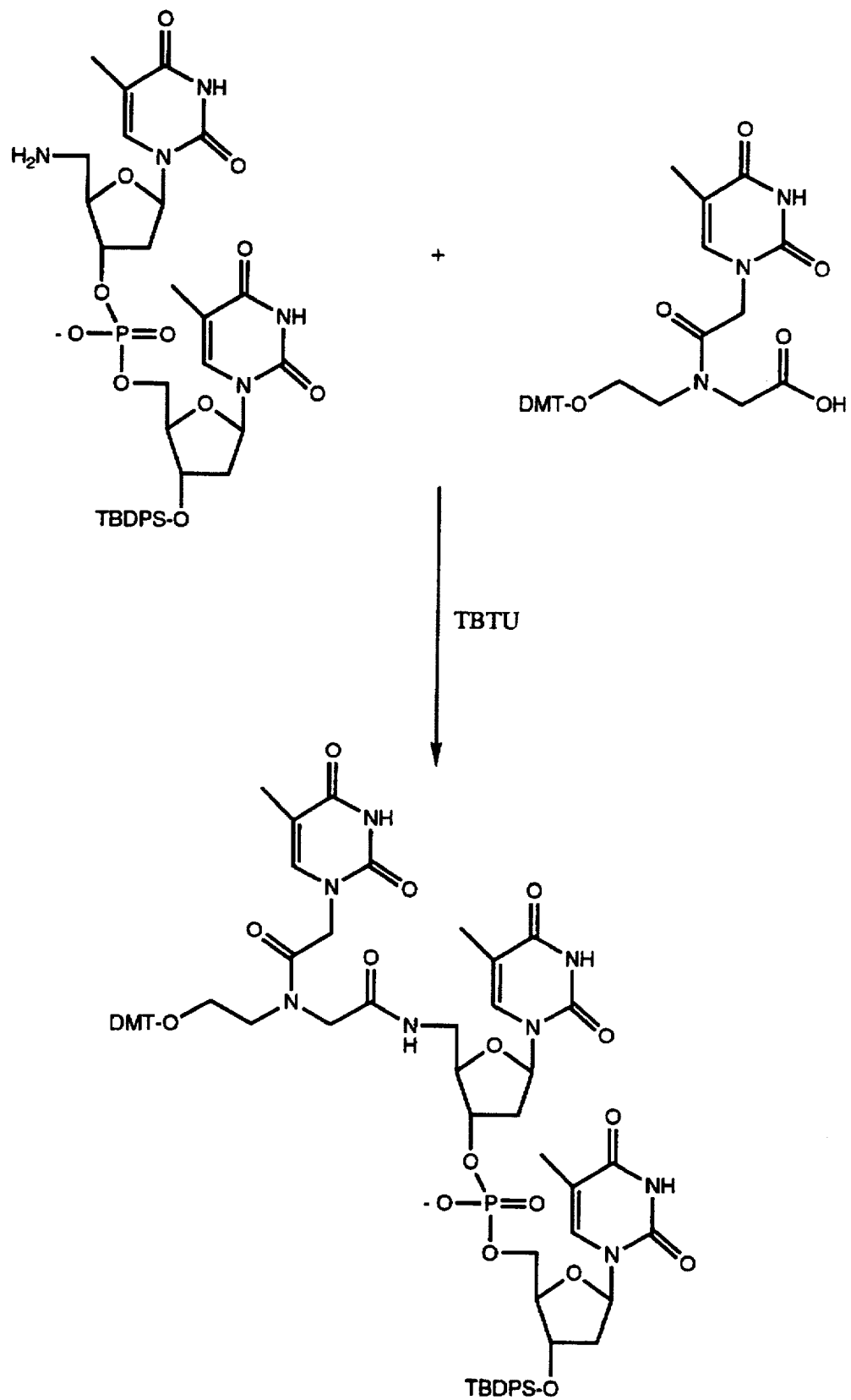
FIG. 4 is a chemical schematic illustrating solution phase synthesis of certain compounds of the invention.
Figure 5:
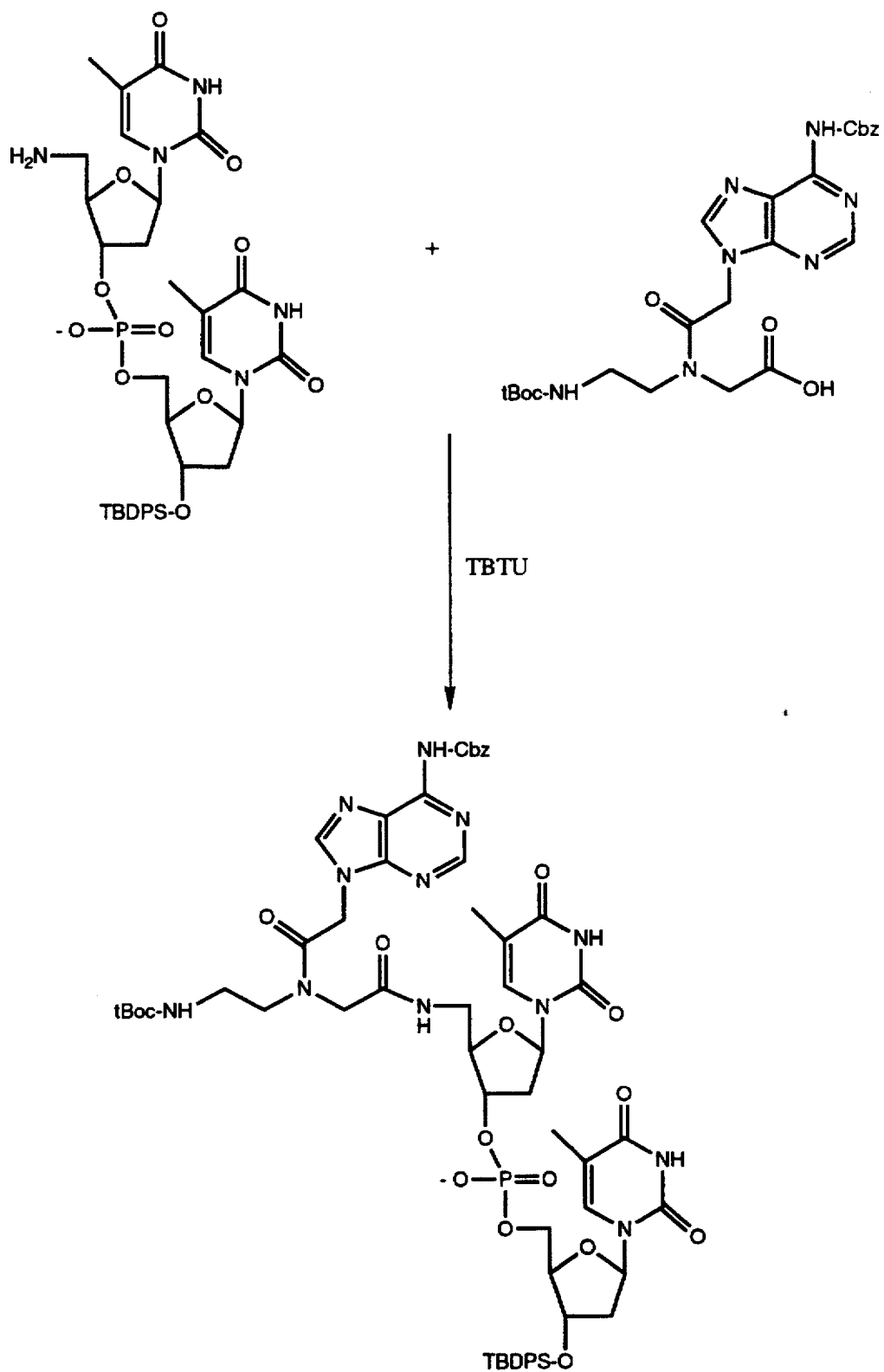
FIG. 5 is a chemical schematic illustrating solid phase synthesis of certain compounds of the invention.
Figure 6:
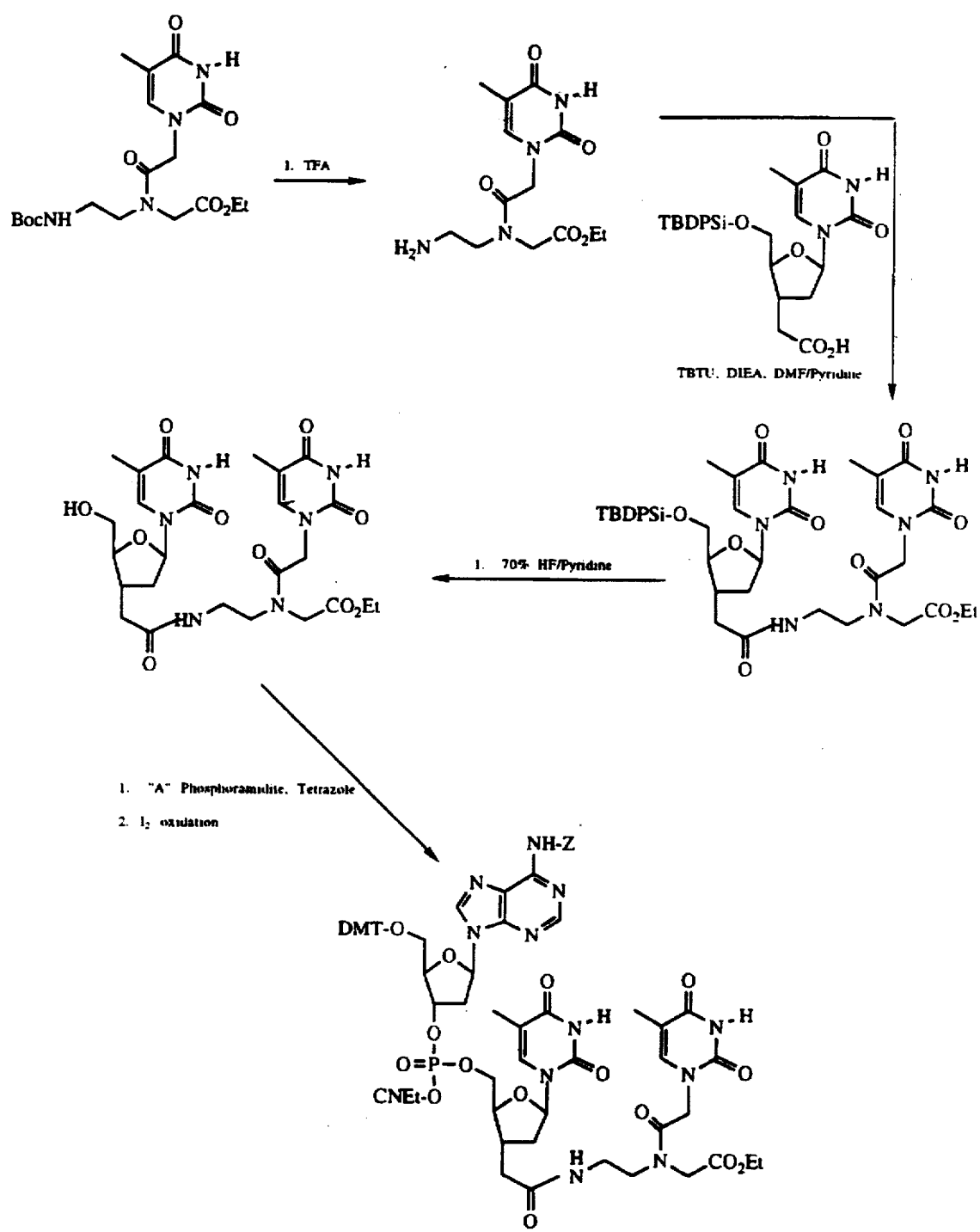
FIG. 6 is a chemical schematic illustrating solution phase synthesis of certain compounds of the invention.

Compounds of the invention can be prepared via both solid phase synthesis or solution phase synthesis. Both methods are illustrated in the examples. Shown in the examples, in Example 1 is a general synthetic preparation of the 2'-deoxyoligonucleotide portion of the macromolecules of the invention. The schemes of Examples 2, 3 and 4 are illustrated in FIG. 1. Example 2 illustrates describes loading of the carboxy terminus of the right side PNA portion of the macromolecule to a solid support resin. Example 3 describes elongation of this right side PNA portion of the macromolecule and formation of an amide linkage to a first 2'-deoxynucleotide via a 3'-carboxy nucleoside. Example 4 illustrates the elongation of the central 2'-deoxyoligonucleotide portion of the macromolecule including addition of 5'-aminonucleotide to effect an amide linkage to the second PNA (left side) portion of the macromolecule. The schemes of Examples 5 and 6 are shown in FIG. 2. Example 5 shows completion of the left side PNA portion. Example 6 illustrated removal of the blocking groups and removal from the resin. The scheme of Example 7 is shown in FIG. 3. Example 7 illustrates the formation of a solution phase DNA linkages for positioning of a 5'-amino-3'-nucleotide as the 5'-terminal nucleotide. The schemes of Examples 8 and 9 are shown in FIGS. 4 and 5, respective. Example 8 illustrates solution phase the solution phase coupling of a PNA portion of a macromolecule of the invention to the DNA portion. In this example, the oligonucleotide of Example 7 is coupled to a first "T" PNA subunit; whereas, in Example 9 a first "A" PNA subunit is coupled to the 2'-deoxyoligonucleotide portion of the macromolecule. The schemes of Examples 10, 11 and 12 are shown in FIG. 6. Example 10, 11 and 12 are illustrative of the solution phase coupling of a DNA portion of a macromolecule of the invention to a PNA portion.

In the below examples the subunits, irrespective of whether they are peptide nucleic acid (PNA) groups or 2'-deoxynucleotides (DNA) groups, the subunits are identified using the standard capital one letter designations, i.e. A, G, C or T. Such designation is indicative of the nucleobase incorporated in to the subunits. Thus "A" is used both to identify a 2'-deoxyadenosine nucleotide as well as a peptide nucleic acid subunit that include an adenine base. For the peptide nucleic acid subunit the adenine base is attached to the N-(2-aminoethyl)glycine backbone via carboxymethyl linker. A standard nucleotide linkage, i.e., phosphodiester, phosphorothioate, phosphorodithioate or phosphoroselenate, is indicated by a hyphen (-) between two adjacent identification letters, e.g. A-T indicates an adenosine nucleotide linked to a thymidine nucleotide. To indicate a peptide nucleic acid linkage either a "(p)" or a "(pna)" are utilized, e.g. A(p)-T indicates an adenine peptide nucleic acid unit attached to a thymine peptide nucleic acid unit.

Transition linkages between 2'-deoxynucleotides and peptide nucleic acid units are indicated in brackets. Thus "T-(3'-carboxy)-A" indicated a thymidine nucleoside having a carboxy group at its 3' position that is linked to the amine moiety of the 2-aminoethyl portion of adenine peptide nucleic acid subunit. Whereas "A-(5'-amino)-T" would indicate a thymidine nucleotide having an amine at its 5' position that is linked to the carboxyl moiety of the glycine portion of the adjacent thymine peptide nucleic acid subunit. Terminal groups, e.g. carboxy, hydroxyl, N-acetylglycine and the like, are indicated using appropriate symbolic nomenclature.

Carbobenzoxy blocking groups are shown as a superscript Z, e.g., $^Z$. Phenoxyacetyl protecting group are shown as a superscript PAC, e.g., $^{PAC}$. As alternatives for the standard polystyrene Merrifield resin described, a highly cross-linked polystyrene sold by Pharmacia or a polyethyleneglycol/ polystyrene graft copolymer called Tentagel sold by Rapp Polymere might be used. To conveniently remove the macromolecules of the invention, the glycine should be attached to the resin via an ester linkage.

The following examples and procedures illustrate the present invention and are not intended to limit the same.

EXAMPLE 1

Oligonucleotide synthesis

Oligonucleotide portions of the macromolecules of the invention are synthesized on an automated DNA synthesizer (Applied Biosystems model 380B) using standard phosphoramidate chemistry with oxidation by iodine. For phosphorothioate oligonucleotides, the standard oxidation bottle is replaced by 0.2M solution of 3H-1,2-benzodithiole-3-one 1,1-dioxide in acetonitrile for the step wise thiation of the phosphite linkages. The thiation wait step was increased to 68 sec and was followed by the capping step. Unless otherwise indicated, after cleavage from the CPG column and deblocking in concentrated ammonium hydroxide at 55° C. (18 hr), the oligonucleotides are purified by precipitation twice out of 0.5M NaCl solution with 2.5 volumes ethanol. Analytical gel electrophoresis is effected in 20% acrylamide, 8M urea, 454 mM Tris-borate buffer, pH=7.0. Phosphodiester and phosphorothioate oligonucleotides are judged from polyacrylamide gel electrophoresis as to material length.

EXAMPLE 2

Low Load t-butyloxycarbonylglycyl Merrifield resin

Hydroxymethyl polystyrene resin (1 g, 650 micromoles hydroxyl/g) was placed in a solid-phase peptide synthesis vessel and washed sequentially (1 minute shaking for each wash) with dichloromethane (DCM, 2 times 10 mL), N,N-dimethylformamide (DMF, 2 times 10 mL), and acetonitrile (2 times 40 mL). To a round-bottom flask was added N-t-butyloxycarbonylglycine (701 mg, 4 mmoles) and O-(benzotriazol-1-yl)-1,1,3,3-tetramethyluronium tetrafluoroborate (1.156 g, 3.6 mmoles). Anhydrous acetonitrile (40 mL) was added to the vial followed by N,N-diisopropylethylamine (1.392 mL, 8 mmoles). The flask was shaken until all solids were dissolved. After one minute the contents of the vial were added to the peptide synthesis vessel and shaken for 125 minutes. The reaction solution was then drained away and the support washed with acetonitrile (1 times 40 mL), pyridine (2 times 40 mL) and DMF (2 times 40 mL). A solution of 10% (v/v) acetic anhydride in DMF (40 mL total volume) was added to the resin and the reaction shaken for 40 minutes. After draining off the reaction solution, the acetic anhydride cap was repeated as above. At the end of the second capping reaction the resin was washed with DMF (2 times 40 mL), pyridine (1 times 40 mL), and DCM (3 times 40 mL). The resin was then dried by blowing with argon.

The extent of glycine derivatization was determined by a quantitative ninhydrin assay. An aliquot of the above resin (50 mg) was placed in a solid-phase peptide synthesis vessel and washed with DCM (2 times 3 mL). The resin was then treated three times with a solution of 5% (v/v) m-cresol in trifluoroacetic acid (3 mL) with shaking for two minutes each time. After draining off the third reaction solution, the resin was washed with DCM (3 times 3 mL), pyridine (3 times 3 mL), and DCM (3 times 3 mL). The resin was then dried by blowing with argon.

An aliquot (5 mg) of the deprotected dried resin was placed in a test tube. To the resin were added a solution of 70% (v/v) water/pyridine (80 microL), Kaiser reagent 1 (100 microL, 200 micromolar KCN in 2% H$_2$O/pyridine), reagent 2 (40 microL, 5% [w/v] ninhydrin in n-BuOH), and reagent 3 (50 microliters, 80% [w/v] phenol in n-BuOH). The reaction was heated at 100° C. for 10 minutes, cooled and diluted with 60% (v/v) EtOH (7 mL). The absorbance at 570 nm was then compared to a control reaction containing no resin and to a standard curve based on quantitation of glycine ethyl ester. A derivatization level of 100 micromoles glycine per gram resin was obtained.

EXAMPLE 3

5'-Hydroxy-T(3'-carboxy)-T(p)-$C^z$(p)-$A^z$(p)-$G^z$(p)-Gly-O-Resin t-Butyloxycarbonylglycyl Merrifield resin (200 mg, 10 microequivalents, example 1) is placed in a solid-phase peptide synthesis vessel. The support is washed with 50% DMF/DCM (4 times 5 mL) and then treated twice with 5% m-cresol in trifluoroacetic acid (4 mL) with shaking for two minutes each time. The support is washed again with 50% DMF/DCM (4 times 5 mL) and then with pyridine (5 times 5 mL). To a vial are added $N^2$-benzyloxycarbonyl-1-(t-butyloxycarbonyl-aminoethylglycyl)guanine (80 micromoles) and O-(benzotriazol-1-yl)-1,1,3,3-tetramethyluronium tetrafluoroborate (72 micromoles). N,N-Dimethylformamide (0.4 mL) and pyridine (0.4 mL) are added to the vial followed by N,N-diisopropylethylamine (160 micromoles). The vial is shaken until all solids are dissolved. After one minute the contents of the vial are added to the peptide synthesis vessel and shaken for 20 minutes. The reaction solution is then drained away and the support washed with pyridine (4 times 5 mL). Remaining free amine is capped by addition of a 10% solution of N-benzyloxycarbonyl-N'-methylimidazole triflate in N,N-dimethylformamide (0.8 mL). After shaking for five minutes, the capping solution is drained and the support washed again with pyridine (4 times 5 mL).

The deprotection, coupling, and capping as described in the above paragraph are repeated with three additional PNA monomers: $N^6$-benzyloxycarbonyl-1-(t-butyloxycarbonyl-aminoethylglycyl)adenine, $N^4$-benzyloxycarbonyl-1-(t-butyloxycarbonyl-aminoethylglycyl)cytosine, and 1-(t-butyloxycarbonylaminoethylglycyl)thymine.

The deprotection, coupling, and capping are then repeated once more, but the monomer used in this case is 5'-(tertbutyldiphenylsilyl)-3'-carboxymethylthymidine. After the capping reaction, the resin is washed with pyridine (3 times 3 mL) and DMF (3 times 3 mL). Anhydrous THF (3 mL) is added to the flask followed by 45 microL of 70% (v/v) HF/pyridine. After shaking overnight the resin is washed with THF (5 times 3 mL), DMF (3 times, 3 mL), acetonitrile (5 times 3 mL), and DCM (5 times 3 mL). The resin is then dried by blowing with argon.

EXAMPLE 4

T(5'-amino)-$G^{PAC}$-$C^{PAC}$-$A^{PAC}$-T-T(3'-carboxy)-T(p)-$C^z$(p)-$A^z$(p)-$G^z$(p)-Gly-O-Resin 5'-Hydroxy-T(3'-carboxy)-$G^z$(p)-$C^z$(p)-$A^z$(p)-T(p)-Gly-O-Resin (10 microequivalents, example 3) is placed in a DNA synthesis column. Standard DNA synthesis (Example 1) is performed with phosphoramidites containing phenoxyacetyl protecting groups on the exocyclic amines, 2-cyanoethyl groups on the phosphorous, and 4,4'-dimethoxytrityl groups on the 5'-hydroxyl. The 5'-terminal phosphoramidite coupled is 5'-(monomethoxytritylamino)thymidine-3'-(N,N-diisopropylamino-2-cyanoethyl) phosphoramidite. The monomethoxytrityl group is removed by the standard automated treatment with dichloroacetic acid in DCM. After washing with DCM, the resin is dried under reduced pressure.

EXAMPLE 5

N-Acetylglycyl-T(p)-T(p)-$C^z$(p)-T(p)-$C^z$(p)-$G^z$(p)-Cz(p)-COOH

Hydroxymethyl polystyrene resin (115 mg, 75 microequivalents) was placed in a solid-phase peptide synthesis vessel. The support was washed with DCM (3 times 3 mL), DMF (3 times 3 mL), pyridine (3 times 3 mL), and DMF again (2 times 3 mL). To a vial was added $N^4$-benzyloxycarbonyl-1-(t-butyloxycarbonyl-aminoethylglycyl)cytosine (151 mg, 300 micromoles) and O-(benzotriazol-1-yl)-1,1,3,3-tetramethyluronium tetrafluoroborate (87 mg, 270 micromoles). N,N-Dimethylformamide (1.25 mL) and pyridine (1.25 mL) were added to the vial followed by N,N-diisopropylethylamine (105 microL, 600 micromoles). The vial was shaken until all solids were dissolved. After one minute the contents of the vial were added to the peptide synthesis vessel and shaken for 30 minutes. The reaction solution was then drained away and the support washed with DMF (4 times 3 mL). The coupling of the C monomer was repeated as above. The resin was then capped by addition of 10% N-benzyloxycarbonyl-N'-methyl-imidazole triflate in N,N-dimethylformamide (2.25 mL) followed by shaking for 5 minutes. The resin was finally washed with pyridine (4 times 3 mL) and was then ready for chain extension.

The support was washed with 50% DMF/DCM (4 times 3 mL) and then treated twice with 5% m-cresol in trifluoroacetic acid (3 mL) with shaking for two minutes each time. The support was washed again with 50% DMF/DCM (4 times 3 mL) and then with pyridine (5 times 3 mL). To a vial were added $N^2$-benzyloxycarbonyl-1-(t-butyloxycarbonyl-aminoethylglycyl)guanine (163 mg, 300 micromoles) and O-(benzotriazol-1-yl)-1,1,3,3-tetramethyluronium tetrafluoroborate (87 mg, 270 micromoles). N,N-Dimethylformamide (1.25 mL) and pyridine (1.25 mL) were added to the vial followed by N,N-diisopropylethylamine (105 microL, 600 micromoles). The vial was shaken until all solids were dissolved. After one minute the contents of the vial were added to the peptide synthesis vessel and shaken for 20 minutes. The reaction solution was then drained away and the support washed with pyridine (5 times 3 mL). Remaining free amine was capped by addition of a 10% solution of N-benzyloxycarbonyl-N'-methyl-imidazole triflate in N,N-dimethylformamide (2.25 mL). After shaking for five minutes, the capping solution was drained and the support washed again with pyridine (4 times 3 mL).

The deprotection, coupling, and capping as described in the above paragraph were repeated in the following order with the PNA monomers: $N^4$-benzyloxycarbonyl-1-(t-butyloxycarbonylaminoethylglycyl)cytosine, and 1-(t-butyloxycarbonyl-aminoethylglycyl)thymine, $N^4$-benzyloxycarbonyl-1-(t-butyloxycarbonylaminoethylglycyl)cytosine, 1-(t-butyloxycarbonyl-aminoethylglycyl)thymine, 1-(t-butyloxycarbonylaminoethylglycyl)thymine, and then with N-acetylglycine. After the last capping reaction, the resin was washed with pyridine (5 times 3 mL) and DCM (4 times 3 mL). The resin was then dried by blowing with argon.

A portion (29 mg, 10 microequivalents) of the resin was placed in a solid phase peptide synthesis vessel and tetrahydrofuran (2.5 mL) was added, followed by a solution of aqueous saturated potassium bicarbonate (0.25 mL) and tetrabutylammonium hydrogen sulphate (34 mg, 100 micromoles). The reaction was then shaken for 14 hours at room temperature. Water (1 mL) was added to the reaction, causing precipitation of a white solid. The liquid was filtered off and saved. The resin and white solid were then washed with additional water (1 mL) which was added to the first wash. Concentration to dryness under reduced pressure resulted in a white solid mixed with a pink oil. Water (6 mL) was added and the pH was adjusted to 2 with solid $KHSO_4$. The liquid and suspended yellow solid were then transferred to Eppendorf tubes and the solid was spun down. The solvent was removed and the residual yellow solid was redissolved in 30% acetonitrile in water containing 0.1% TFA. Reverse phase chromatography resulted in the desired product (2.6 mg, 1 micromole): molecular mass=2498 (electrospray mass spectrometry).

EXAMPLE 6

N-Acetylglycyl-T(p)-T(p)-C(p)-T(p)-C(p)-G(p)-C(p)-T(5'-amino)-G-C-A-T-T(3'-carboxy)-T(p)-C(p)-A(p)-G(p)-Gly-COOH T (5'-Amino)-$G^{PAC}$-$C^{PAC}A^{PAC}$-T-T(3'-carboxy)-T(p)-$C^Z$(p)-$A^Z$(p)-$G^Z$(p)-Gly-O-resin (5 microequivalents, Example 3) is placed in a solid-phase peptide synthesis vessel. The resin is washed with DCM (3 times 3 mL), DMF (3 times 3 mL), and pyridine (3 times 3 mL). To a vial are added N-Acetylglycyl-T(p)-T(p)-$C^Z$(p)-T(p)-$C^Z$(p)-$G^Z$(p)-$C^Z$(p)-COOH (10 micromoles, prepared as in example 5) and O-(benzotriazol-1-yl)-1,1,3,3-tetramethyluronium tetrafluoroborate (9 micromoles). N,N-Dimethylformamide (0.3 mL) and pyridine (0.3 mL) are added to the vial followed by N,N-diisopropylethylamine (20 micromoles). The vial is shaken until all solids are dissolved. After one minute the contents of the vial are added to the peptide synthesis vessel and shaken for 4 hours. The reaction solution is then drained away and the support washed five times with pyridine.

Tetrahydrofuran (2 mL) is added to the resin, followed by a solution of aqueous saturated potassium bicarbonate (0.2 mL) and tetrabutylammonium hydrogen sulphate (27 mg, 80 micromoles). The reaction is shaken for 14 hours at room temperature. The solution is then drained and kept. The resin is washed with 50% tetrahydrofuran/water (3 times 1 mL) and with water (3 times 2 mL). The wash solutions are added to the reaction solution and concentrated under reduced pressure to remove organics—concentration is stopped at a final volume of 2 milliliters. Inorganics are removed by gel filtration. The crude material is dissolved in aqueous 15 mM acetic acid (10 mL) and alternately degassed under vacuum and back-filled with nitrogen four times. Palladium on $BaSO_4$ (5%, 30 mg) is added and the solution is stirred at RT °C. for 2 hours. The catalyst is removed by filtration and the product is then purified by reverse phase HPLC.

EXAMPLE 7

5'-Amino-deoxythymidylyl-(3'-5')-3'-O-tertbutyldiphenylsilyldeoxythymidine ($H_2$N-T-T)

3'-tertButyldiphenylsilyldeoxythymidine (58 mg, 120 micromoles) and 5'-(p-methoxytriphenylmethylamino)-3'-[O-(2-cyanoethyl)-N,N-diisopropylaminophosphoramidyl] deoxythymidine (71 mg, 100 micromoles) were put in separate 10 mL round-bottom flasks and each co-evaporated once with anhydrous pyridine (2 mL) and twice with anhydrous acetonitrile (1.5 mL). The compounds were then each dissolved in anhydrous acetonitrile (0.75 mL) and combined. The reaction was initiated by the addition of a solution of 0.4M 1H-tetrazole in anhydrous acetonitrile (1 mL, 400 micromoles tetrazole). After stirring 50 minutes at room temperature the reaction was quenched by pouring into an oxidizing solution (10 mL of 0.43% 12 in 90.54% THF, 0.41% pyridine, and 9.05% water).

The oxidation reaction was stirred an additional 40 minutes and poured into a separatory funnel containing dichloromethane (50 mL) and water (20 mL). Residual iodine was removed by washing the organic layer with a solution of 0.3% sodium metabisulfite in water (95 mL). The organic layer was then concentrated to a yellow oil by rotary evaporation under reduced pressure. The yellow oil was co-evaporated with toluene (2×15 mL) under reduced pressure to remove residual pyridine.

The crude material was then dissolved in dichloromethane (6 mL) and the trityl group was removed by addition of a solution of 3% trichloroacetic acid in dichloromethane (3 mL). After stirring 15 minutes at room temperature the reaction was quenched by pouring into a separatory funnel containing cold (4° C.) saturated aqueous sodium bicarbonate (10 mL). Additional dichloromethane (20 mL) was added and the organic layer was separated. A residual emulsion in the aqueous layer was broken up by addition of more dichloromethane (20 mL). The two organic layers were then combined and concentrated to dryness under reduced pressure. The desired product was purified from the resulting crude tan solid by preparative silica TLC run in 20% (v/v) ethanol/chloroform, 0.2% N,N-diisopropylethylamine (49 mg, 63 micromoles, 63%): $R_f$ (20% (v/v) ethanol/chloroform, 0.2% N,N-diisopropylethylamine)=0.05; $^1$H NMR (200 MHz, MeOH-d4) d 7.65 (m, 4H), 7.4 (m, 8H), 6.45 (m, 1H), 5.95 (m, 1H), 4.6 (m, 1H), 4.1 (m, 2H), 3.9 (m, 1H), 3.6 (m, 1H), 3.2 (m, 1H), 2.9 (m, 2H), 2.5–2.0 (m, 1.89 (s, 6H), 1.1 (s, 9H); $^{31}$P NMR (MeOH-d4) d 0.85; ESMS m/e 782.

EXAMPLE 8

N,N-Diisopropylethylammonium salt of DMTO-O-T(pna)-CONH-T-T $H_2$N-TpT (25 mg, 30 micromoles) was dissolved in 1:1 DMF/pyridine (0.8 mL). To a separate vial were added 1-[O-4,4,dimethoxytrityl-hydroxyethylglycyl)thymine (23.5 mg, 40 micromoles) and O-(benzotriazol-1-yl)-1,1,3,3-tetramethyluronium tetrafluoroborate (11.6 mg, 36 micromoles). The vial's contents were dissolved in 1:1 DMF/pyridine (0.8 mL) and N,N-diisopropylethylamine (14 microL, 80 micromoles). After 5 minutes the activated ester solution was added to the $H_2$N-TpT solution. The reaction was stirred at room temperature for 80 minutes and quenched by the addition of ethyl alcohol (0.5 mL). After an additional 150 minutes the reaction mixture was concentrated to dryness under reduced pressure. The resulting solid was purified by preparative silica TLC run in 20% (v/v) ethanol/chloroform, 0.2% N,N-diisopropylethylamine (27 mg, 20 micromoles, 67%): $R_f$ (20% (v/v) ethanol/chloroform, 0.2% N,N-diisopropylethylamine)=0.18; $^1$H NMR (200 MHz, DMSO-d6) d 11.35 (m, 3H), 8.95 (br s, 0.3H), 8.72 (br s, 0.7H), 7.79 (m, 2H), 7.61–7.19 (m, 22H), 6.91 (m, 4H), 6.36 (m, 1H), 6.03 (m, 1H), 4.78 (m, 2H), 4.59 (s, 1H), 4.41 (m, 3H), 4.20 (s, 1H), 3.93 (m, 2H), 3.65 (s, 2H), 3.18 (br s, 3H), 2.97 (m, 2H), 3.74 (s, 6H), 3.42 (m, 4H), 2.01 (br s, 4H), 1.77 (m, 7H), 1.62 (s, 2H), 1.03 (m, 15H); $^{13}$C NMR (DMSO-d6): 167.9, 164.6, 163.8, 158.2, 150.5, 144.9, 143.0, 136.1, 135.7, 132.9, 130.2, 129.8, 128.1, 127.8, 126.8, 123.4, 118.6, 113.4, 110.7, 110.1, 107.9, 86.3, 84.0, 83.0, 74.8, 74.5, 61.3, 56.2, 55.1, 47.5, 26.8, 18.7, 12.1; $^{31}$P NMR (DMSO-d6) d −0.2, −1.05; ESMS m/e 1351.

EXAMPLE 9

N,N-Diisopropylethylammonium salt of tBoc-A$^Z$(pna)-CONH-T-T

H$_2$N-TpT (19 mg, 24 micromoles) was dissolved in 1:1 DMF/pyridine (0.65 mL). To a separate vial were added N$^6$-benzyloxycarbonyl-1-(t-butyloxycarbonyl-aminoethylglycyl)adenine (12.7 mg, 24 micromoles) and O-(benzotriazol-1-yl)-1,1,3,3-tetramethyluronium tetrafluoroborate (7.1 mg, 22 micromoles). The vial's contents were dissolved in 1:1 DMF/pyridine (0.65 mL) and N,N-diisopropylethylamine (8.4 microL, 48 micromoles). After 2 minutes the activated ester solution was added to the H$_2$N-TpT solution. The reaction was stirred at room temperature for 105 minutes and quenched by the addition of ethyl alcohol (0.5 mL). After an additional 120 minutes the reaction mixture was concentrated to dryness under reduced pressure. The resulting solid was purified by preparative silica TLC run in 20% (v/v) ethanol/chloroform, 0.2% N,N-diisopropylethylamine (6 mg, 5 micromoles, 21%): R$_f$ (20% (v/v) ethanol/chloroform, 0.2% N,N-diisopropylethylamine)=0.07; $^1$H NMR (200 MHz, DMSO-d6) d 11.37 (s, 1H), 11.22 (s, 1H), 10.64 (br s, 1H), 9.17 (br s, 0.3H), 8.90 (br s, 0.7H), 8.59 (m, 2H), 8.30 (m, 1H), 7.80 (M, 1H), 7.58 (S, 3H), 7.38 (m, 12H), 7.16 (m, 1H), 6.36 (m, 1H), 6.04 (m, 1H), 5.43 (m, 1H), 5.32 (s, 1H), 5.23 (s, 2H), 5.1 (s, 1H), 4.42 (m, 3H), 4.19 (m, 1H), 3.98 (s, 1H), 3.87 (m, 3H), 3.77 (m, 1H), 3.66 (m, 1H), 3.02 (m, 2H), 2.68 (m, 1H), 2.03 (m, 4H), 1.74 (m, 6H), 1.02 (m, 30H); $^{31}$P NMR (DMSO-d6) d −0.01, −0.8.

EXAMPLE 10

1-(t-Butyloxycarbonyl-aminoethylglycyl)thymine, ethyl ester 1-(t-butyloxycarbonyl-aminoethylglycyl)thymine (300 mg, 780 micromoles) was dissolved in 50% DMF/pyridine (3.0 mL) and N,N-diisopropylethylamine (0.25 mL, 1.44 mmoles) was added. After stirring 5 minutes O-(benzotriazol-1-yl)-1,1,3,3-tetramethyluronium tetrafluoroborate (350 mg, 1.1 mmoles) was added to give light orange solution. The reaction was stirred 30 minutes after which absolute ethanol (0.75 mL, 4.26 mmoles) was added. After stirring an additional 90 minutes the reaction mixture was concentrated to an oil under reduced pressure. The oil was dissolved in ethyl acetate (30 mL) and cooled to 5° C. The pure product precipitated as a white solid which was collected by filtration (289 mg, 701 micromoles, 90%):; $^1$H NMR (200 MHz, CDCl13) d 8.33 (br s, 1H), 7.02 (s, 0.3H), 6.97 (s, 0.7H), 5.58 (m, 1H), 4.59 (s, 1.4H), 4.43 (s, 0.6H), 4.1 (s, 2H), 3.54 (m, 2H), 3.33 (m, 2H), 1.92 (s, 3H), 1.47 (s, 9H).

EXAMPLE 11

TBDPS-T-CONH-T(pna)-OEt

The ethyl ester of 1-(t-Butyloxycarbonyl-aminoethylglycyl)thymine (30 mg, 72 microMol) was dissolved in 1.0 mL of trifluoroacetic acid and stirred at RT for 30 minutes. This was concentrated in vacuo and then co-evaporated with 5 mL of toluene twice. The 5'-O-tertbutyldiphenylsilyl-3'-carboxymethyldeoxyribothymidine (25 mg, 48 microMol) was dissolved in 0.400 mL of a 1:1 DMF/pyridine solution. To this solution was added TBTU (21 mg, 65 microMol) and N,N-diisopropyl ethyl amine (25 microL, 144 microMol). The reaction became a pale orange color and was stirred for 30 minutes. The amine from the TFA deprotection step was dissolved in 0.6 mL of DMF/Pyridine, added to the activated carboxythymidine solution and stirred at room temperature for one hour. TLC analysis (20% MeOH/DCM) indicated that all of the activated acid was consumed. The solution was concentrated in vacuo to an oil. The oil was purified on a 2 mm preparative TLC Plate (20 mm×20 mm) with 20% MeOH/DCM as the eluting solvent. The least polar fraction contained the PNA-DNA chimera providing the desired product as a white solid (25 mg, 36 micromoles 50%); $^1$H NMR (200 MHz, CDCl$_3$) d 9.8 (br s, 1H), 9.6 (br s, 1H), 7.7 (m, 4H), 7.3 (m, 9H), 7.0 (dd, 1H), 6.2 (m, 1H), 4.5–3.4 (12H), 2.9 (m, 1H), 2.5–2.1 (m, 4H), 1.5 (s, 3H), 1.3 (d, 6H), 1.1 (s, 9H); $^{13}$C NMR (CDCl$_3$): d11.764, 12.083, 12.391, 14.144, 26.796, 27.055, 29.708, 35.232, 37.177, 37.788, 38.932, 48.298, 61.486, 64.854, 84.476, 85.018, 111.110, 127.711, 129.980, 135.407, 135.654, 140.976, 150.835, 151.555, 167.416, 172.192; ESMS m/e 817.

EXAMPLE 12

T-CONH-T(pna)-OEt

The above dimer (30 mg, 0.058 mMol) was desilylated by dissolving in 1 ml dry THF and cooled to 0° C. To this was added 20 mL of 70% HF/Pyridine and 10 mL of a 1M solution of tetrabutyl ammonium fluoride was added and the reaction mixture stirred overnight. TLC (10% MeOH/DCM) indicated the reaction was complete. The solution was quenched with 1 ml of saturated NaHCO$_3$ and stirred until the gas evolution ceased. The aqueous layer was diluted with an additional 5 ml of water and extracted 2× with 3 ml of ethyl acetate. The organic layers were combined and discarded. The aqueous layer was evaporated to dryness resulting in a mixture of the deprotected dimer and NaHCO$_3$. The mixture was suspended in methanol and purified on two 20×20 0.5 mm preparative TLC plates eluting with 30% ethanol in chloroform. After the plates finished eluting, they were dried and the fluorescent band scraped and extracted. The extract was filtered and evaporated to yield 12 mg (56% yield) of the deprotected dimer that was contaminated with a small amount of tetrabutylammonium fluoride. $^1$H(CD$_4$OD): 1.0–1.5 (mm, 10H); 1.5 (m, 2H); 1.9 (s, 6H); 2.1–2.8 (mm, 6H); 3.2–4.0 (mm, 15H); 4.1–4.4 (m, 4H); 4.7 (s, 1H); 6.1 (m, 1H); 7.3 (s, 1H); 8.0 (s, 1H).

EXAMPLE 13

(5'-DMT)-A$^Z$-T-(3'-carboxy)-T(pna) (including cyanoethoxy protected phosphodiester linkage)

The deprotected dimer of Example 12 (12 mg, 0.0207 mmol) was co-evaporated twice with anhydrous pyridine and twice with anhydrous acetonitrile. The resulting white solid was dissolved in 3 ml of 1:1 acetonitrile:DMF. To this solution was added 1 ml of a 0.1M solution of adenosine phosphoramidite and 1 ml of 0.4M 1H-tetrazole solution. This was stirred at ambient temperature for 1 hr, and then an additional 1 ml of amidite was added and stirring continued for an additional hour. At the end of that time 10 ml of oxidizing solution (0.43% I$_2$ in 90.54% THF, 0.41% pyridine, and 9.05% water) was added and the reaction stirred for 1 hour. The reaction was quenched with 25 ml of a 1M solution of sodium bisulfite solution. This solution was extracted with chloroform 2×20 ml and the combined extracts were washed with another 25 ml portion of bisulfite solution, resulting in a slightly yellow organic phase. The choroform solution was dried over magnesium sulfate and concentrated to a yellow oil. The mixture was purified using 20×20 cm preparative TLC plates (2, 0.5 mm coating) eluting with 20% acetone in dichloromethane. The diastereomeric mixture of trimer was isolated as an oil weighing 25 mg for a 93% yield; $^1$H (CDCl$_3$): 1.2 (m, 13H); 2.5–3.2 (mm 5H); 3.4 (m, 4H); 3.7 (s, 6H); 4.1 (m, 1H); 4.4 (m, 1H); 5.2 (m, 1H); 6.5 (m, 1H); 6.8 (m, 4H); 7.3 (m, 10H); 7.5 (m, 3H); 8.0 (d, 2 H); 8.2 (d, 2H); 8.7 (s, 1H); 9.1 (s, 1H); $^{31}$P (CDCl$_3$): 8.247, 8.116.

EXAMPLE 14

Stability of PNA oligomers to NH$_4$OH deprotection conditions

In the first case a PNA oligomer containing a free amino terminus (H-TAT-TCC-GTC-ATC-GCT-CCT-CA-Lys-NH$_2$) (all PNA) was dissolved in 70% concentrated NH$_4$OH. The reaction was incubated at 23° C. and aliquots were examined by reverse phase HPLC at the time points indicated below. In the second experiment a PNA oligomer with a glycyl-capped amino terminus (H-Gly-TGT-ACG-TCA-CAA-CTA-Lys-NH$_2$) (all PNA) was dissolved in 90% concentrated NH$_4$OH and heated in a sealed flask at 55° C.

The NH$_4$OH stability of the PNA oligomer containing a free amino terminus was insufficient to allow the removal of base protecting groups from the PNA/DNA chimera. Capping the amino terminus with a glycyl group greatly increased the stability of the PNA to aqueous base. The glycyl-capped PNA demonstrated only minimal degradation at the 11 hour time point with 15% decomposition after 23 hours. The glycyl capped PNA is completely stable to conditions used to remove the phenoxyacetyl protecting group and relatively stable to those used for the standard DNA base protecting groups (benzoyl and isobutyryl amides). The results are shown in Table 1.

TABLE 1

| hours | Remaining uncapped PNA, 23° C. | Remaining capped PNA, 55° C. |
|---|---|---|
| 1 | 97 | 100 |
| 2 | 92 | 99 |
| 4 | 85 | |
| 5 | | 97 |
| 6 | 75 | |
| 8 | 60 | |
| 11 | | 92 |
| 23 | | 85 |

EXAMPLE 15

Macromolecule Having Peptide Nuclei Acids Regions Flanking A Central 2'-Deoxy Phosphorothioate Oligonucleotide Region Joined via Amine and Ester linkages A first region of peptide nucleic acids is prepared as per Example 2 above. The peptide nucleic acids is prepared from the C terminus towards the N terminus using monomers having protected amine groups. Following completion of the first peptide region, the terminal amine blocking group is removed and the resulting amine reacted with a 3'-C-(formyl)-2',3'-dideoxy-5'-trityl nucleotide prepared as per the procedure of Vasseur, et. al., *J. Am. Chem. Soc.* 1992, 114, 4006. The condensation of the amine with the aldehyde moiety of the C-formyl nucleoside is effected as per the conditions of the Vasseur, ibid., to yield an intermediate imine linkage. The imine linkage is reduced under reductive alkylation conditions of Vasseur, ibid., with HCHO/NaBH$_3$CN/AcOH to yield the nucleoside connected to the peptide nucleic acid via an methyl alkylated amine linkage. An internal 2'-deoxy phosphorothioate nucleotide region is then continued from this nucleoside as per the protocols of Example 1. Peptide synthesis for the second peptide region is commenced by reaction of the carboxyl end of the first peptide nucleic acid of this second region with the 5' hydroxy of the last nucleotide of the DNA region following removal of the dimethoxytrityl blocking group on that nucleotide. Coupling is effected via EDC in pyridine to form an ester linkage between the peptide and the nucleoside. Peptide synthesis is then continued to complete the second peptide nucleic acid region.

EXAMPLE 16

Macromolecule Having Peptide Nucleic Acids Regions Flanking A Central 2'-Deoxy Phosphoroselenate Oligonucleotide Region The synthesis of Example 15 is repeated except for introduction of the phosphoroselenate linkages in the 2'-deoxynucleotide portion of the macromolecule, oxidization is effected with 3H-1,2-benzothiaseleno-3-ol as per the procedure reported by Stawinski, et al., *Tenth International Roundtable: Nucleosides, Nucleotides and Their Biological Evaluation*, Sep. 16–20, 1992, Abstracts of Papers, Abstract 80.

EXAMPLE 17

Macromolecule Having Peptide Nucleic Acids Regions Flanking A Central 2'-Deoxy Phosphorodithioate Oligonucleotide Region The synthesis of Example 15 is repeated except for introduction of the phosphorodithioate linkages in the 2'-deoxynucleotide portion of the macromolecule, oxidization is effected utilizing the procedures of Beaton, et. al., Chapter 5, Synthesis of oligonucleotide phosphorodithioates, page 109, *Oligonucleotides and Analogs, A Practical Approach*, Eckstein, F., Ed.; The Practical Approach Series, IRL Press, New York, 1991.

PROCEDURE 1 ras-Luciferase Reporter Gene Assembly

The ras-luciferase reporter genes were assembled using PCR technology. Oligonucleotide primers were synthesized for use as primers for PCR cloning of the 5'-regions of exon 1 of both the mutant (codon 12) and non-mutant (wild-type) human H-ras genes. The plasmids pT24-C3, containing the c-H-ras1 activated oncogene (codon 12, GGC→GTC), and pbc-N1, containing the c-H-ras proto-oncogene, were obtained from the American Type Culture Collection (Bethesda, Md.). The plasmid pT3/T7 luc, containing the 1.9 kb firefly luciferase gene, was obtained from Clontech Laboratories (Palo Alto, CA). The oligonucleotide PCR primers were used in standard PCR reactions using mutant and non-mutant H-ras genes as templates. These primers produce a DNA product of 145 base pairs corresponding to sequences −53 to +65 (relative to the translational initiation site) of normal and mutant H-ras, flanked by NheI and HindIII restriction endonuclease sites. The PCR product was gel purified, precipitated, washed and resuspended in water using standard procedures.

PCR primers for the cloning of the *P. pyralis* (firefly) luciferase gene were designed such that the PCR product would code for the full-length luciferase protein with the exception of the amino-terminal methionine residue, which would be replaced with two amino acids, an amino-terminal lysine residue followed by a leucine residue. The oligonucleotide PCR primers used for the cloning of the luciferase gene were used in standard PCR reactions using a commercially available plasmid (pT3/T7-Luc) (Clontech), containing the luciferase reporter gene, as a template. These primers yield a product of approximately 1.9 kb corresponding to the luciferase gene, flanked by unique HindIII and BssHII restriction endonuclease sites. This fragment was gel purified, precipitated, washed and resuspended in water using standard procedures.

To complete the assembly of the ras-luciferase fusion reporter gene, the ras and luciferase PCR products were digested with the appropriate restriction endonucleases and cloned by three-part ligation into an expression vector containing the steroid-inducible mouse mammary tumor virus promotor MMTV using the restriction endonucleases NheI, HindIII and BssHII. The resulting clone results in the insertion of H-ras 5' sequences (−53 to +65) fused in frame with the firefly luciferase gene. The resulting expression vector encodes a ras-luciferase fusion product which is expressed under control of the steroid-inducible MMTV promoter. These plasmid constructions contain sequences encoding amino acids 1–22 of activated (RA2) or normal (RA4) H-ras proteins fused in frame with sequences coding for firefly luciferase. Translation initiation of the ras-luciferase fusion mRNA is dependent upon the natural H-ras AUG codon. Both mutant and normal H-ras luciferase fusion constructions were confirmed by DNA sequence analysis using standard procedures.

PROCEDURE 2

Transfection of Cells with Plasmid DNA

Transfections were performed as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds., John Wiley and Sons, N.Y.,) with the following modifications. HeLa cells were plated on 60 mm dishes at $5\times10^5$ cells/dish. A total of 10 μg or 12 μg of DNA was added to each dish, of which 1 μg was a vector expressing the rat glucocorticoid receptor under control of the constitutive Rous sarcoma virus (RSV) promoter and the remainder was ras-luciferase reporter plasmid. Calcium phosphate-DNA coprecipitates were removed after 16–20 hours by washing with Tris-buffered saline [50 Mm Tris-Cl (pH 7.5), 150 mM NaCl] containing 3 mM EGTA. Fresh medium supplemented with 10% fetal bovine serum was then added to the cells. At this time, cells are pre-treated with the macromolecules of the invention prior to activation of reporter gene expression by dexamethasone.

PROCEDURE 3

Treatment of Cells

Following plasmid transfection, cells are washed with phosphate buffered saline prewarmed to 37° C. and Opti-MEM containing 5 μg/mL N-[1-(2,3-dioleyloxy)propyl]-N,N,N,-trimethylammonium chloride (DOTMA) is added to each plate (1.0 ml per well). Test compounds are added from 50 μM stocks to each plate and incubated for 4 hours at 37° C. Medium is removed and replaced with DMEM containing 10% fetal bovine serum and the appropriate test compound at the indicated concentrations and cells are incubated for an additional 2 hours at 37° C. before reporter gene expression is activated by treatment of cells with dexamethasone to a final concentration of 0.2 μM. Cells are harvested and assayed for luciferase activity fifteen hours following dexamethasone stimulation.

PROCEDURE 4

Luciferase Assays

Luciferase is extracted from cells by lysis with the detergent Triton X-100 as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, N.Y. A Dynatech ML1000 luminometer is used to measure peak luminescence upon addition of luciferin (Sigma) to 625 μM. For each extract, luciferase assays are performed multiple times, using differing amounts of extract to ensure that the data is gathered in the linear range of the assay.

PROCEDURE 5

Melting Curves

Absorbance vs temperature curves are measured at 260 nm using a Gilford 260 spectrophotometer interfaced to an IBM PC computer and a Gilford Response II spectrophotometer. The buffer contained 100 mM $Na^+$, 10 mM phosphate and 0.1 mM EDTA, pH 7. Test compound concentration is 4 μM for each strand determined from the absorbance at 85° C. and extinction coefficients calculated according to Puglisi and Tinoco, *Methods in Enzymol.* 1989, 180, 304–325. $T_m$ values, free energies of duplex formation and association constants are obtained from fits of data to a two state model with linear sloping baselines. Petersheim, M. and Turner, D. H., *Biochemistry* 1983, 22, 256–263. Reported parameters are averages of at least three experiments. For some test compounds, free energies of duplex formation are also obtained from plots of $T_m^{-1}$ vs $\log_{10}$ (concentration). Borer, P. N., Dengler, B., Tinoco, L., Jr., and Uhlenbeck, O. C., *J. Mol. Biol.*, 1974, 86, 843–853.

PROCEDURE 6

Gel Shift Assay

The structured ras target transcript, a 47-nucleotide hairpin containing the mutated codon 12, is prepared and mapped as described in Lima et al., *Bio-chemistry* 1991, 31, 12055–12061. Hybridization reactions are prepared in 20 μl containing 100 mM sodium, 10 mM phosphate, 0.1 mM EDTA, 100 CPM of T7-generated RNA (approximately 10 pM), and test compound ranging in concentration from 1 pM to 10 μM. Reactions are incubated 24 hours at 37° C. Following hybridization, loading buffer was added to the reactions and reaction products are resolved on 20% native polyacrylamide gels, prepared using 45 mM tris-borate and 1 mM $MgCl_2$ (TBM). Electrophoresis is carried out at 10° C. and gels are quantitated using a Molecular Dynamics Phosphorimager.

PROCEDURE 7

RNase H Analysis

RNase H assays are performed using a chemically synthesized 25-base oligoribonucleotide corresponding to bases +23 to +47 of activated (codon 12, G→U) H-ras mRNA. The 5' end-labeled RNA is used at a concentration of 20 nM and incubated with a 10-fold molar excess of test compound in a reaction containing 20 mM tris-Cl, pH 7.5, 100 mM KCl, 10 mM $MgCl_2$, 1 mM dithiothreitol, 10 μg tRNA and 4 U RNasin in a final volume of 10 μl. The reaction components are preannealed at 37° C. for 15 minutes then allowed to cool slowly to room temperature. HeLa cell nuclear extracts are used as a source of mammalian RNase H. Reactions are initiated by addition of 2 μg of nuclear extract (5 μl) and reactions are allowed to proceed for 10 minutes at 37° C.

Reactions are stopped by phenol/chloroform extraction and RNA components are precipitated with ethanol. Equal CPMs are loaded on a 20% polyacrylamide gel containing 7M urea and RNA cleavage products are resolved and visualized by electrophoresis followed by autoradiography. Quantitation of cleavage products is performed using a Molecular Dynamics Densitometer.

PROCEDURE 8 ras Transactivation Reporter Gene System

The expression plasmid pSV2-oli, containing an activated (codon 12, GGC→GTC) H-ras cDNA insert under control of the constitutive SV40 promoter, was a gift from Dr. Bruno Tocque (Rhone-Poulenc Sante, Vitry, France). This plasmid is used as a template to construct, by PCR, a H-ras expression plasmid under regulation of the steroid-inducible mouse mammary tumor virus (MMTV) promoter. To obtain H-ras coding sequences, the 570 bp coding region of the H-ras gene is amplified by PCR. The PCR primers are designed with unique restriction endonuclease sites in their 5'-regions to facilitate cloning. The PCR product containing the coding region of the H-ras codon 12 mutant oncogene is gel purified, digested, and gel purified once again prior to cloning. This construction is completed by cloning the insert into the expression plasmid pMAMneo (Clontech Laboratories, CA).

The ras-responsive reporter gene pRDO53 is used to detect ras expression. Owen et al., *Proc. Natl. Acad. Sci. U.S.A.* 1990, 87, 3866–3870.

PROCEDURE 9

Northern blot analysis of ras expression in vivo

The human urinary bladder cancer cell line T24 is obtained from the American Type Culture Collection (Rockville Md.). Cells are grown in McCoy's 5A medium with L-glutamine (Gibco BRL, Gaithersburg Md.), supplemented with 10% heat-inactivated fetal calf serum and 50 U/ml each of penicillin and streptomycin. Cells are seeded on 100 mm plates. When they reached 70% confluency, they are treated with test compound. Plates are washed with 10 ml prewarmed PBS and 5 ml of Opti-MEM reduced-serum medium containing 2.5 µl DOTMA. Test compound is then added to the desired concentration. After 4 hours of treatment, the medium is replaced with McCoy's medium. Cells are harvested 48 hours after test compound treatment and RNA is isolated using a standard CsCl purification method. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, N.Y.

The human epithelioid carcinoma cell line HeLa 229 is obtained from the American Type Culture Collection (Bethesda, Md.). HeLa cells are maintained as monolayers on 6-well plates in Dulbecco's Modified Eagle's medium (DMEM) supplemented with 10% fetal bovine serum and 100 U/ml penicillin. Treatment with test compound and isolation of RNA are essentially as described above for T24 cells.

Northern hybridization: 10 µg of each RNA is electrophoresed on a 1.2% agarose/formaldehyde gel and transferred overnight to GeneBind 45 nylon membrane (Pharmacia LKB, Piscataway, N.J.) using standard methods. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, N.Y. RNA is UV-crosslinked to the membrane. Double-stranded $^{32}$P-labeled probes are synthesized using the Prime a Gene labeling kit (Promega, Madison Wis.). The ras probe is a SalI-NheI fragment of a cDNA clone of the activated (mutant) H-ras mRNA having a GGC-to-GTC mutation at codon-12. The control probe is G3PDH. Blots are prehybridized for 15 minutes at 68° C. with the Quick-Hyb hybridization solution (Stratagene, La Jolla, Calif.). The heat-denatured radioactive probe ($2.5 \times 10^6$ counts/2 ml hybridization solution) mixed with 100 µl of 10 mg/ml salmon sperm DNA is added and the membrane is hybridized for 1 hour at 68° C. The blots are washed twice for 15 minutes at room temperature in 2× SSC/0.1% SDS and once for 30 minutes at 60° C. with 0.1× SSC/0.1%SDS. Blots are autoradiographed and the intensity of signal is quantitated using an ImageQuant PhosphorImager (Molecular Dynamics, Sunnyvale, Calif.). Northern blots are first hybridized with the ras probe, then stripped by boiling for 15 minutes in 0.1× SSC/0.1%SDS and rehybridized with the control G3PDH probe to check for correct sample loading.

PROCEDURE 10

Inhibition of proliferation of cancer cells and use as controls for chemotherapeutic agent test Cells are cultured and treated with test compound essentially as described in Example 9. Cells are seeded on 60 mm plates and are treated with test compound in the presence of DOTMA when they reached 70% confluency. Time course experiment: On day 1, cells are treated with a single dose of test compound at a final concentration of 100 nM. The growth medium is changed once on day 3 and cells are counted every day for 5 days, using a counting chamber. Dose-response experiment: Various concentrations of test compound (10, 25, 50, 100 or 250 nM) are added to the cells and cells are harvested and counted 3 days later. The active compounds of the invention can then be used standards in this same screen for screening of other chemotherapeutic agents.

---

What is claimed is:

1. A macromolecule of the structure:

PNA-DNA-PNA wherein:

said DNA of said PNA-DNA-PNA comprises at least one 2'-deoxynucleotide; and each of said PNAs of said PNA-DNA-PNA comprise at least one peptide nucleic acid subunit having formula (I):

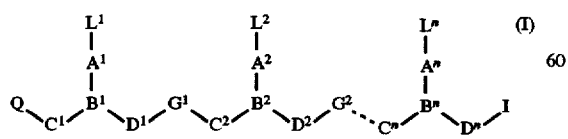

wherein n is at least 2, each of $L^1$ and $L^n$ is independently selected from the group consisting of hydrogen, hydroxy, $(C_1-C_4)$ alkanoyl, nucleobases, aromatic moieties, DNA intercalators, nucleobase-binding groups, heterocyclic moieties, and reporter ligands, at least one of $L^1$ to $L^n$ being a nucleobase, a DNA intercalator, or a nucleobase-binding group;

each of $R^3$ and $R^4$ is independently selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino;

each of $C^1$ to $C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR^3R^4$ and $SR^5$, where $R^3$ and $R^4$ are as defined above, and $R^5$ is hydrogen, $(C_1-C_6)$alkyl, hydroxy-, alkoxy-, or alkylthio-substituted $(C_1-C_6)$alkyl, or $R^6$ and $R^7$, together, are alicyclic or heterocyclic;

each of $D^1$ to $D^n$ is $(CR^6R^7)_z$ where $R^6$ and $R^7$ are as defined above;

each of y and z is zero or an integer from 1 to 10, the sum y+z being greater than 2 but not more than 10;

each of $G^1$ to $G^{n-1}$ is —$NR^3CO$—, —$NR^3CS$—, —$NR^3SO$— —$NR^3SO_2$—, —$CONR^3$—, —$CSNR^3$—, —$SONR^3$— or —$SO_2NR_3$— where $R^3$ is as defined above;

each pair of $A^1$ to $A^n$ and $B^1$ to $B^n$ are selected such that:
 (a) A is a group of formula (IIa), (IIb) or (IIc) and B is N or $R^3N^+$; or
 (b) A is a group of formula (IId) and B is CH;

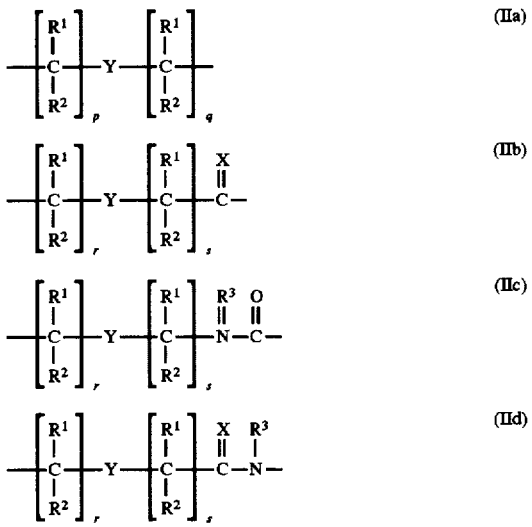

where:
X is O, S, Se, $NR^3$, $CH_2$ or $C(CH_3)_2$;
Y is a single bond, O, S or $NR^4$;
each of p and q is zero or an integer from 1 to 5, the sum p+q being not more than 10;
each of r and s is zero or an integer from 1 to 5, the sum r+s being not more than 10;
each $R^1$ and $R^2$ is independently selected from the group consisting of hydrogen, ($C_1$–$C_4$)alkyl which may be hydroxy- or alkoxy- or alkylthio-substituted, hydroxy, alkoxy, alkylthio, amino and halogen;

Q is —$CO_2H$, —CONR'R'', —$SO_3H$ or —$SO_2NR'R''$ or an activated derivative of —$CO_2H$ or —$SO_3H$; and I is —NR'''R'''' or —NR'''C(O)R'''';

where:
R', R'', R''', and R'''' are independently selected from the group consisting of hydrogen, alkyl, amino protecting groups, reporter ligands, intercalators, chelators, peptides, carbohydrates, lipids, steroids, nucleosides, nucleotides, nucleotide diphosphates, nucleotide triphosphates, oligonucleotides, oligonucleosides and soluble and non-soluble polymers, provided that at least one R' is said DNA of said PNA-DNA-PNA and at least one R'''' is said DNA of said PNA-DNA-PNA.

2. A macromolecule of the structure:

PNA-DNA or DNA-PNA wherein:
said DNA of said PNA-DNA or DNA-PNA comprises at least one 2'-deoxynucleotide; and
said PNA of said PNA-DNA or DNA-PNA comprises at least one peptide nucleic acid subunit having formula (I):

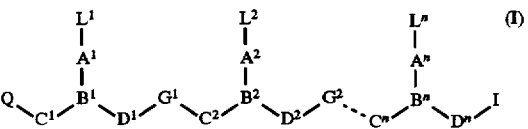

wherein:
n is at least 2, each of $L^1$ to $L^n$ is independently selected from the group consisting of hydrogen, hydroxy, ($C_1$–$C_4$)alkanoyl, nucleobases, aromatic moieties, DNA intercalators, nucleobase-binding groups, heterocyclic moieties, and reporter ligands, at least one of $L^1$ to $L^n$ being a nucleobase, a DNA intercalator, or a nucleobase-binding group;

each of $R^3$ and $R^4$ is independently selected from the group consisting of hydrogen, ($C_1$–$C_4$)alkyl, hydroxy- or alkoxy- or alkylthio-substituted ($C_1$–$C_4$)alkyl, hydroxy, alkoxy, alkylthio and amino;

each of $C^1$ to $C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined above, and $R^5$ is hydrogen, ($C_1$–$C_6$)alkyl, hydroxy-, alkoxy-, or alkylthio-substituted ($C_1$–$C_6$)alkyl, or $R^6$ and $R^7$, together, are alicyclic or heterocyclic;

each of $D^1$ to $D^n$ is $(CR^6R^7)_z$ where $R^6$ and $R^7$ are as defined above;

each of y and z is zero or an integer from 1 to 10, the sum y+z being greater than 2 but not more than 10;

each of $G^1$ to $G^{n-1}$ is —$NR^3CO$—, —$NR^3CS$—, —$NR^3SO$— —$NR^3SO_2$—, —$CONR^3$—, —$CSNR^3$—, —$SONR^3$— where $R^3$ is as defined above;

each pair of $A^1$ to $A^n$ and $B^1$ to $B^n$ are selected such that:
 (a) A is a group of formula (IIa), (IIb) or (IIc) and B is N or $R^3N^+$; or
 (b) A is a group of formula (IId) and B is CH;

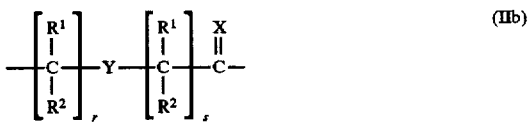

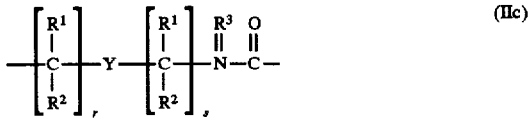

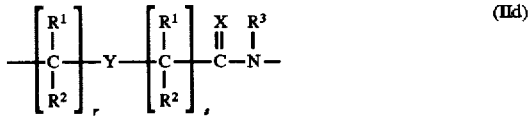

where
X is O, S, Se, $NR^3$, $CH_2$ or $C(CH_3)_2$;
Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1-C_4)$alkyl which may be hydroxy- or alkoxy- or alkylthio- substituted, hydroxy, alkoxy, alkylthio, amino and halogen;

Q is —$CO_2H$, —CONR'R", —$SO_3H$ or —$SO_2$NR'R" or an activated derivative of —$CO_2H$ or —$SO_3H$; and I is —NR'''R"" or —NR'''C(O)R"";

2'-deoxynucleotides linked together in a sequence by phosphodiester, phosphorothioate or phosphorodithioate linkages.

10. A macromolecule of claim 2 wherein said PNA of said PNA-DNA or DNA-PNA comprises a compound having a formula selected from the group consisting of IIIa, IIIb and IIIc:

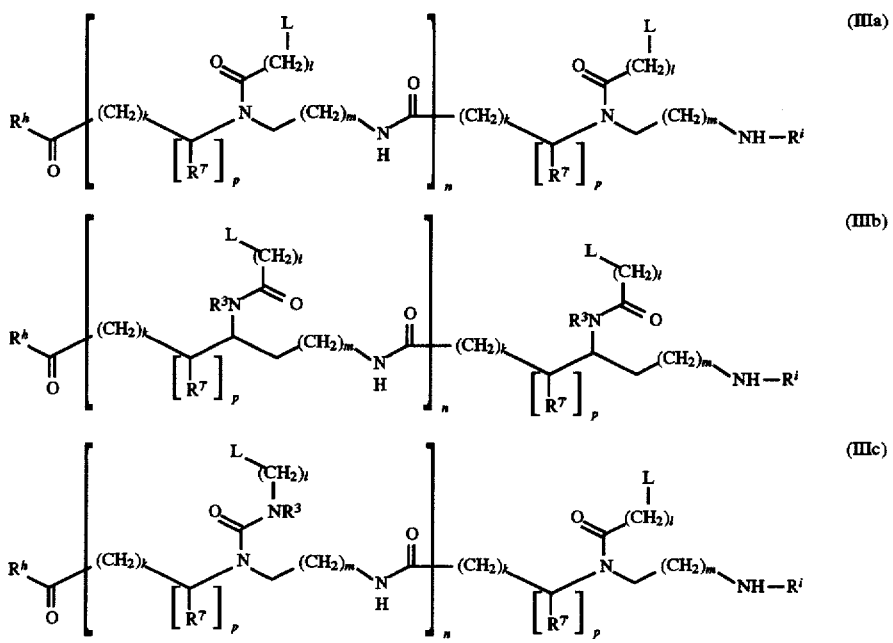

where:
R', R", R''', and R"" are independently selected from the group consisting of hydrogen, alkyl, amino protecting groups, reporter ligands, intercalators, chelators, peptides, carbohydrates, lipids, steroids, nucleosides, nucleotides, nucleotide diphosphates, nucleotide triphosphates, oligonucleotides, oligonucleosides and soluble and non-soluble polymers, provided that R' is said DNA of said PNA-DNA or DNA-PNA or R"" is said DNA of said PNA-DNA or DNA-PNA.

3. The macromolecule of claim 2 having the structure PNA-DNA.

4. The macromolecule of claim 2 having the structure DNA-PNA.

5. A macromolecule of claim 2 wherein said PNA-DNA or DNA-PNA macromolecule hybridizes to a strand of nucleic acid.

6. A macromolecule of claim 5 wherein said strand of nucleic acid is a RNA strand.

7. A macromolecule of claim 2 wherein:
said DNA of said PNA-DNA or DNA-PNA includes at least three 2'-deoxynucleotides linked together in a sequence: and
said PNA of said PNA-DNA or DNA-PNA includes at least two peptide nucleic acid subunits.

8. A macromolecule of claim 2 wherein said 2'-deoxynucleotide is a phosphodiester, a phosphorothioate or a phosphorodithioate 2'-deoxynucleotide.

9. A macromolecule of claim 2 wherein said DNA of said PNA-DNA or DNA-PNA includes at least three wherein:
each L is independently selected from the group consisting of hydrogen, phenyl, heterocyclic moieties, nucleobases;
each $R^7$ is independently selected from the group consisting of hydrogen, and the side chains of naturally occurring alpha amino acids;
n is an integer from 1 to 60;
each of k, l, and m is independently zero or an integer from 1 to 5;
p is zero or 1;
$R^h$ is OH or NR'R"; and
$R^i$ is —R"" or —C(O)R"".

11. A macromolecule of claim 10 where said PNA of said PNA-DNA or DNA-PNA comprises a compound having a formula selected from the group consisting of (IIIa), (IIIb), and (IIIc), wherein each L is independently selected from the group consisting of the nucleobases thymine (T), adenine (A), cytosine (C), guanine (G) and uracil (U), k and m are zero or 1, and n is an integer from 1 to 30.

12. A compound of claim 11 wherein:
said DNA of said PNA-DNA or DNA-PNA includes at least three of said 2'-deoxynucleotides linked together in a sequence;
said PNA of said PNA-DNA or DNA-PNA includes at least two peptide nucleic acid subunits; and
said 2'-deoxynucleotides are joined via phosphodiester, phosphorothioate or phosphorodithioate linkages.

13. A macromolecule of claim 2 wherein said PNA of said PNA-DNA or DNA-PNA is covalently bound to said DNA of said PNA-DNA or DNA-PNA with an amide, amine or ester linkage.

14. A macromolecule of claim 1 wherein said PNA-DNA-PNA macromolecule hybridizes to a strand of nucleic acid.

15. A macromolecule of claim 14 wherein said strand of nucleic acid is a RNA strand.

16. A macromolecule of claim 1 wherein:

said DNA of said PNA-DNA-PNA includes at least three 2'-deoxynucleotides linked together in a sequence: and each PNA of said PNA-DNA-PNA includes at least two peptide nucleic acid subunits.

17. A macromolecule of claim 1 wherein said 2'-deoxynucleotide is a phosphodiester, a phosphorothioate or a phosphorodithioate 2'-deoxynucleotide.

18. A macromolecule of claim 1 wherein said DNA of said PNA-DNA-PNA includes at least three 2'-deoxynucleotides linked together in a sequence by phosphodiester, phosphorothioate or phosphorodithioate linkages.

19. A macromolecule of claim 1 wherein each of said PNAs of said PNA-DNA-PNA comprises a compound having a formula selected from the group consisting of IIIa, IIIb and IIIc:

$R^h$ is OH or NR'R"; and $R^i$ is —R"" or —C(O)R"".

20. A macromolecule of claim 19 where each of said PNAs of said PNA-DNA-PNA comprise a compound having a formula selected from the group consisting of (IIIa), (IIIb), and (IIIc), wherein each L is independently selected from the group consisting of the nucleobases thymine (T), adenine (A), cytosine (C), guanine (G) and uracil (U), k and m are zero or 1, and n is an integer from 1 to 30.

21. A compound of claim 20 wherein:

said DNA of said PNA-DNA-PNA includes at least three of said 2'-deoxynucleotides linked together in a sequence:

each PNA of said PNA-DNA-PNA includes at least two peptide nucleic acid subunits; and said 2'-deoxynucleotides are joined via phosphodiester, phosphorothioate or phosphorodithioate linkages.

22. A macromolecule of claim 1 wherein each of said PNAs of said PNA-DNA-PNA is covalently bound to said DNA of said PNA-DNA-PNA with an amide, amine or ester linkage.

23. A macromolecule of the structure:

PNA-(amide link)-DNA-(amide link)-PNA:

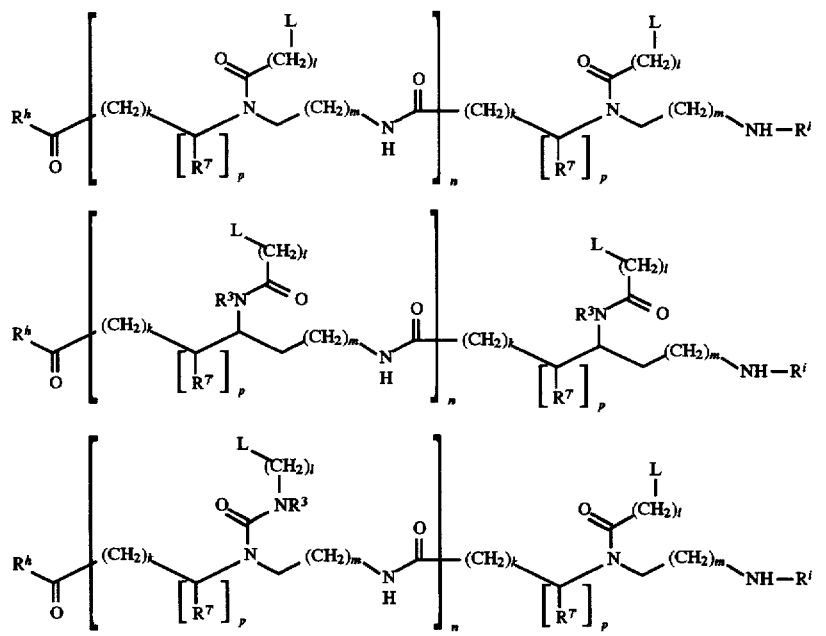

wherein:

each L is independently selected from the group consisting of hydrogen, phenyl, heterocyclic moieties, and nucleobases;

each $R^{7'}$ is independently selected from the group consisting of hydrogen, and the side chains of naturally occurring alpha amino acids;

n is an integer from 1 to 60;

each of k, l, and m is independently zero or an integer from 1 to 5;

p is zero or 1;

wherein:

said DNA of said structure comprises at least one 2'-deoxynucleotide;

each of said PNAs of said structure comprise at least one peptide nucleic acid subunit; and each of said amide links of said structure includes an amide linkage of the structure:

—C(=O)—NH— or —NH—C(=O)—.

* * * * *

UNITED STATES PATENT AND TRADEMARK OFFICE
CERTIFICATE OF CORRECTION

PATENT NO. : 5,700,922
DATED : December 23, 1997
INVENTOR(S) : Phillip Dan Cook

It is certified that error appears in the above-identified patent and that said Letters Patent is hereby corrected as shown below:

Col. 11, line 15, change "$C_2H$" to --$CO_2H$--

Col. 11, line 55, change "ms" to --is-

Col. 20, line 35, change "DMTO-O-T" to --DMT-O-T-

Signed and Sealed this

Eleventh Day of April, 2000

Q. TODD DICKINSON

Attest:

Attesting Officer

Director of Patents and Trademarks

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 10

```
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 1:

TGCATTTCAG                                                                      10

( 2 ) INFORMATION FOR SEQ ID NO: 2:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 2:

TTCTCGCTGC ATTTCAG                                                              17

( 2 ) INFORMATION FOR SEQ ID NO: 3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 3:

TATTCCGTCA TCGCTCCTCA                                                           20

( 2 ) INFORMATION FOR SEQ ID NO: 4:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 4:

TGTACGTCAC AACTA                                                                15
```